(12) United States Patent
Carr et al.

(10) Patent No.: US 12,257,046 B2
(45) Date of Patent: Mar. 25, 2025

(54) RESONANCE FREQUENCY SHIFT SENSORS

(71) Applicant: Iowa State University Research Foundation, Inc., Ames, IL (US)

(72) Inventors: Adam Russell Carr, Ames, IA (US); Nigel Forest Reuel, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 771 days.

(21) Appl. No.: 17/220,393

(22) Filed: Apr. 1, 2021

(65) Prior Publication Data

US 2021/0345917 A1 Nov. 11, 2021

Related U.S. Application Data

(60) Provisional application No. 63/010,349, filed on Apr. 15, 2020.

(51) Int. Cl.
| | |
|---|---|
| *A61B 5/145* | (2006.01) |
| *A61B 5/00* | (2006.01) |
| *G01N 29/02* | (2006.01) |
| *G01N 29/036* | (2006.01) |
| *G01N 29/22* | (2006.01) |
| *G01N 33/487* | (2006.01) |

(52) U.S. Cl.
CPC ...... *A61B 5/14546* (2013.01); *A61B 5/14517* (2013.01); *A61B 5/6804* (2013.01); *G01N 29/022* (2013.01); *G01N 29/036* (2013.01); *G01N 29/222* (2013.01); *G01N 33/487* (2013.01); *G01N 2291/0228* (2013.01)

(58) Field of Classification Search
CPC . A61B 5/14546; A61B 5/6833; A61B 5/6804; A61B 5/14517; A61B 5/4875; A61B 5/0024; A61B 5/4266; A61B 2562/0214; A61B 2562/12; G01N 29/022; G01N 33/487; G01N 29/036; G01N 29/222; G01N 2291/0228
See application file for complete search history.

(56) References Cited

U.S. PATENT DOCUMENTS

| | | | |
|---|---|---|---|
| 11,724,260 B2* | 8/2023 | Wang | B01L 3/502784 436/86 |
| 2003/0175947 A1* | 9/2003 | Liu | B82Y 30/00 422/68.1 |
| 2017/0102345 A1* | 4/2017 | Lei | G01R 33/302 |

(Continued)

OTHER PUBLICATIONS

Gao et al. Fully integrated wearable sensor arrays for multiplexed in situ perspiration analysis. Nature. Jan. 28, 2016; 529 (7587): 509-514.*

(Continued)

*Primary Examiner* — Shogo Sasaki
(74) *Attorney, Agent, or Firm* — Schwegman Lundberg & Woessner, P.A.

(57) ABSTRACT

The present disclosure provides a resonator system for detecting perspiration. The system includes a resonator. The resonator includes an electronically conductive segment. The resonator further includes a polymeric component coating at least a portion of the electronically conductive segment. The resonator further includes a fluidic channel component positioned adjacent to the polymeric component and comprising a microfluidic channel.

17 Claims, 15 Drawing Sheets

(56) References Cited

U.S. PATENT DOCUMENTS

| | | | |
|---|---|---|---|
| 2019/0009190 A1* | 1/2019 | Greene | G01N 27/44791 |
| 2019/0234907 A1* | 8/2019 | Edwards | G01N 29/22 |
| 2019/0234961 A1* | 8/2019 | Gentalen | G01N 30/00 |
| 2019/0374941 A1* | 12/2019 | Winkler | G01N 29/022 |
| 2019/0381507 A1* | 12/2019 | Weiss | G01N 29/222 |
| 2020/0011834 A1* | 1/2020 | Webster | G01N 29/036 |
| 2020/0093416 A1* | 3/2020 | Rogers | A61B 5/002 |
| 2020/0200712 A1* | 6/2020 | Jesorka | G01N 29/222 |
| 2020/0284788 A1* | 9/2020 | Sagle | G01N 33/54346 |
| 2020/0316605 A1* | 10/2020 | Wang | G01N 21/6428 |
| 2021/0345917 A1* | 11/2021 | Carr | A61B 5/14546 |
| 2022/0333052 A1* | 10/2022 | Duan | C12M 23/16 |
| 2022/0347687 A1* | 11/2022 | Duan | C12M 1/42 |
| 2023/0219086 A1* | 7/2023 | Duan | C12M 23/16 422/527 |

OTHER PUBLICATIONS

Huang, Xian, et al., "Stretchable, Wireless Sensors and Functional Substrates for Epidermal Characterization of Sweat", *Small*, 10(15), (2014), 3083-3090.

Nyein, Hnin Y. Y., et al., "A Wearable Microfluidic Sensing Patch for Dynamic Sweat Secretion Analysis", *ACS Sensors*, 3, (2018), 944-952.

Rose, Daniel P., et al., "Adhesive RFID Sensor Patch for Monitoring of Sweat Electrolytes", *IEEE Transactions on Biomedical Engineering*, 62(6), (Jun. 2015), 1457-1465.

Su, Wenjing, et al., "Additively Manufactured Microfluidics-Based "Peel-and-Replace" RF Sensors for Wearable Applications", *IEEE Transactions on Microwave Theory and Techniques*, 64(6), (Jun. 2016).

* cited by examiner

RESONANCE FREQUENCY SHIFT SENSORS

CROSS-REFERENCE TO RELATED APPLICATIONS

This application claims the priority of U.S. Provisional Patent Application No. 63/010,349, titled RESONANCE FREQUENCY SHIFT SENSORS, filed on Apr. 15, 2020, the contents of which are hereby incorporated by reference.

STATEMENT OF GOVERNMENT SUPPORT

This invention was made with Government support under Grant No. EMW-2017-FP-00607 awarded by the United States Department of Homeland Security. The U.S. Government has certain rights in this invention.

BACKGROUND

Determining the presence and activity of perspiration can be useful in many different contexts. However, quantitatively determining the amount of perspiration and salt concentration in the perspiration generated, quickly, can be difficult. Determining these values can help to determine the level of hydration that a person has.

SUMMARY OF THE DISCLOSURE

The present disclosure provides a resonator system for detecting perspiration. The system includes a resonator. The resonator includes an electronically conductive segment. The resonator further includes a polymeric component coating at least a portion of the electronically conductive segment. The resonator further includes a fluidic channel component positioned adjacent to the polymeric component and comprising a microfluidic channel.

The present disclosure further provides a method for making a resonator system. The system includes a resonator. The resonator includes an electronically conductive segment. The resonator further includes a polymeric component coating at least a portion of the electronically conductive segment. The resonator further includes a fluidic channel component positioned adjacent to the polymeric component and comprising a microfluidic channel. The method includes providing or receiving the electronically conductive segment at least partially coated with the polymeric component. The method further includes etching the electronically conductive segment to form a pattern therein. The method further includes adhering the polymeric component to a fluidic channel component precursor. The method further includes forming a microfluidic channel in the fluidic channel component by laser ablation.

BRIEF DESCRIPTION OF THE FIGURES

The drawings illustrate generally, by way of example, but not by way of limitation, various embodiments discussed in the present document.

DETAILED DESCRIPTION

Figure 1:
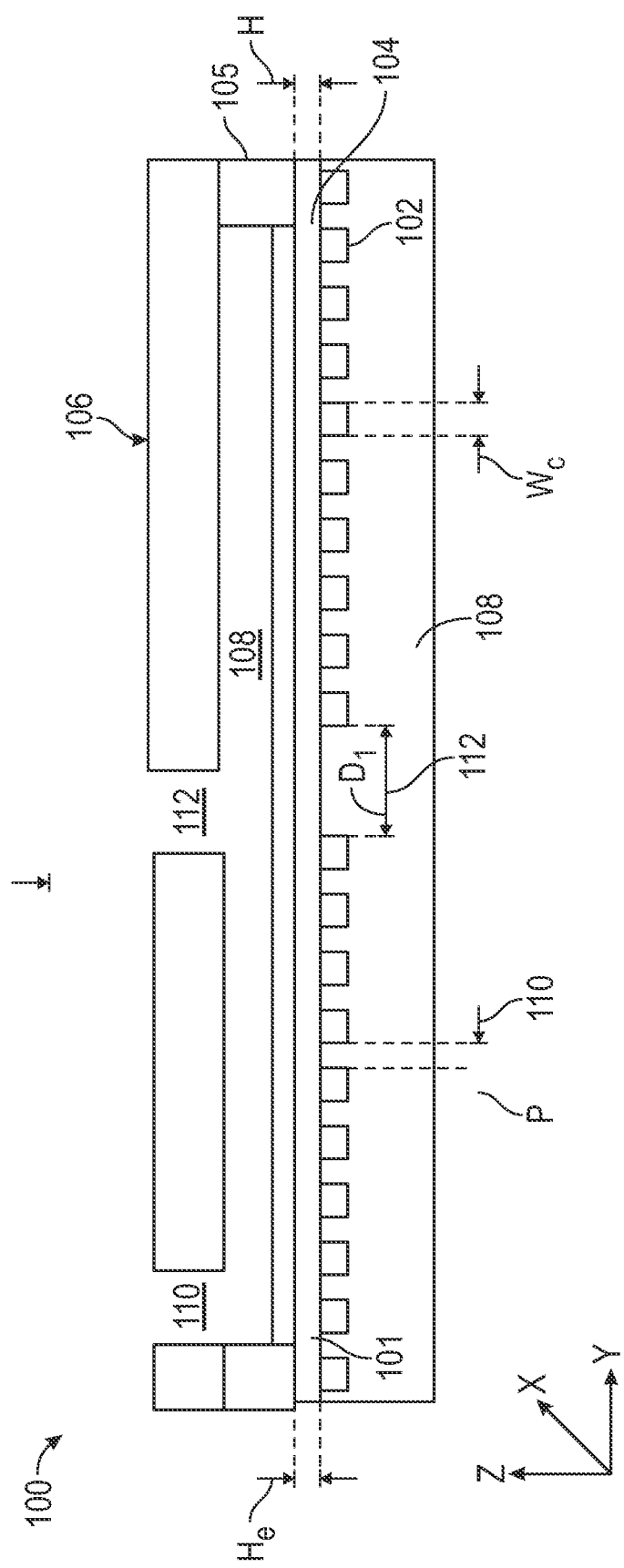
FIG. 1 is a sectional view of resonator system, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0:1% to 0.5%, 1.1% to 2.2%. 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)O$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O) CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to—C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, or cycloalkylalkyl. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl)

is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or trisubstituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, and the like; and R$_3$N wherein each R is independently selected, such as trialkylamines, dialkylarylamines, alkyldiarylamines, triarylamines, and the like. The term "amine" also includes ammonium ions as used herein.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl ($C_1$), ethyl ($C_2$), propyl ($C_3$), or butyl ($C_4$), and $(C_0-C_b)$hydrocarbyl means in certain embodiments there is no hydrocarbyl group.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

As used herein, the term "polymer" refers to a molecule having at least one repeating unit and can include copolymers.

The polymers described herein can terminate in any suitable way. In some embodiments, the polymers can terminate with an end group that is independently chosen from a suitable polymerization initiator, —H, —OH, a substituted or unsubstituted $(C_1-C_{20})$hydrocarbyl (e.g., $(C_1-C_{10})$alkyl or $(C_6-C_{20})$aryl) interrupted with 0, 1, 2, or 3 groups independently selected from —O—, substituted or unsubstituted —NH—, and —S—, a poly(substituted or unsubstituted $(C_1-C_{20})$hydrocarbyloxy), and a poly(substituted or unsubstituted $(C_1-C_{20})$hydrocarbylamino).

Described herein is a resonator system for detecting perspiration. FIG. 1 is a sectional view of resonator system 100. Resonator system 100 includes resonator 101 including electronically conductive segment 102, polymeric component coating 104, adhesive 105, fluidic channel component 106, and microfluidic channel 108.

Figure 2:
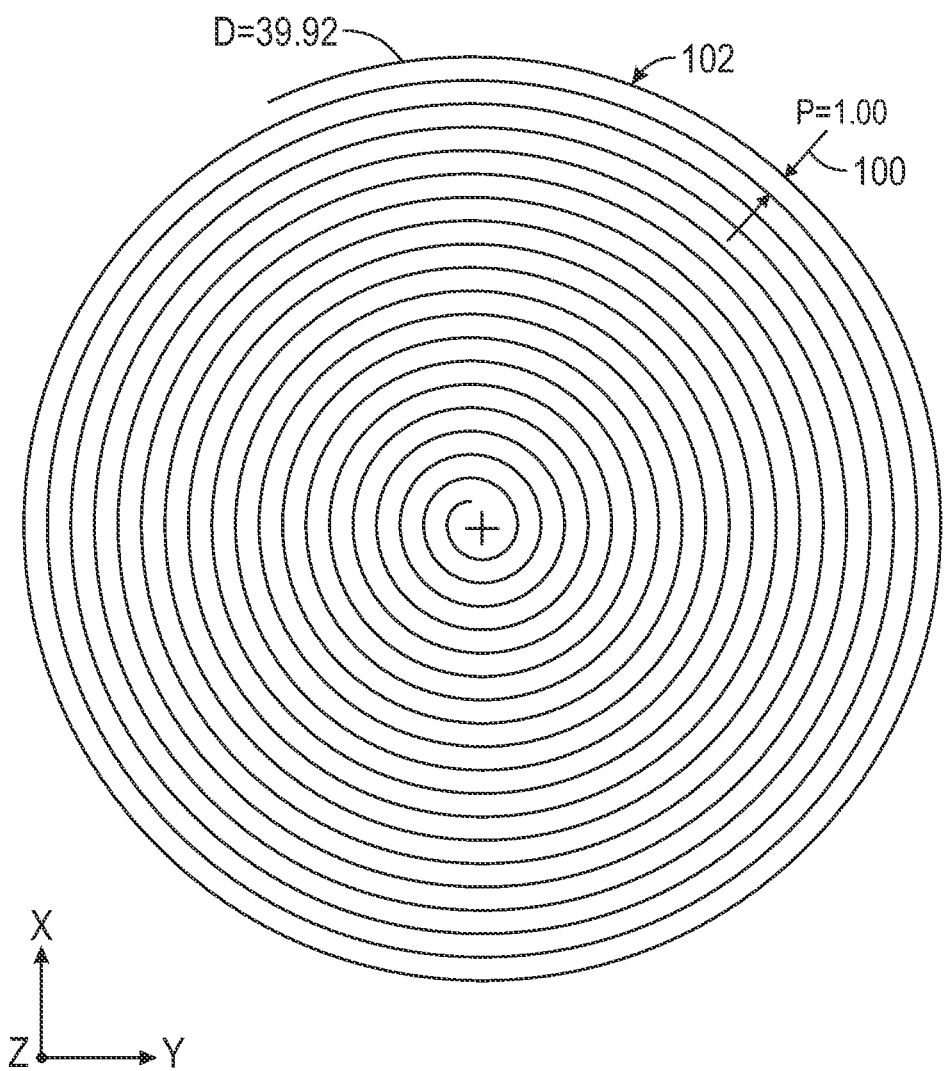
FIG. 2 is a top view of an electronically conductive segment broken away from the resonator of FIG. 1.

Electronically conductive segment 102 includes an electronically conductive metal. FIG. 2 is a top view of electronically conductive segment 102 broken away from the other components of resonator 101 shown in FIG. 1. As shown in FIG. 2, electronically conductive segment 102 includes a plurality of rings. Examples of suitable metals forming electronically conductive segment 102 include copper, silver, gold, aluminum, alloys thereof, or mixtures thereof. Electronically conductive segment 102 can be formed as a continuous segment or may include a plurality of discontinuous segments distributed through resonator 101. Electronically conductive segment 102 can take on any suitable shape or configuration. For example, electronically conductive segment 102 can be configured as a spiral in which adjacent portions or rings of electronically conductive segment 102 are spaced relative to each other defining a pitch therebetween. In some examples, the pitch can be constant across electronically conductive segment 102, thus, as shown, the spiral is an Archimedean spiral.

As shown in FIGS. 1 and 2, electronically conductive segment 102 is continuous. Electronically conductive segment 102 can have any suitable dimensions. For example, a total length of electronically conductive segment can be in a range of from about 5 mm to about 2000 mm, about 15 mm to about 40 mm, about 20 mm to about 25 mm, or less than, equal to, or greater than about 5 mm, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or about 2000 mm. In general, increasing the length of electronically conductive segment 102 decreases the resonance frequency of resonator 101. In embodiments of electronically conductive segment 102, such as that shown in FIGS. 1 and 2, where electronically conductive segment is a spiral the length refers to the total distances measured along electronically conductive segment from end to end.

A distance between opposed faces of adjacent portions of electronically conductive segment 102 is characterized as pitch 110. In some embodiments of conductive segment 102, pitch 110 is constant across all portions. In other embodiments, pitch 110 can be variable. In further embodiments, a first plurality of pitches 110 may be constant while a second plurality of pitches 110 may be variable. For example, as shown in FIG. 1, pitch 110 is less than pitch 112. At each instance, pitch 110 or 112 can be in a range of from about 0.1 mm to about 10 mm, about 1 mm to about 3 mm, or less than, equal to, or greater than about 0.1 mm, 0.5, 1, 1.5, 2, 2.5, 3, 3.5, 4, 4.5, 5, 5.5, 6, 6.5, 7, 7.5, 8, 8.5, 9, 9.5, or about 10 mm. Generally, increasing pitch 110 or 112 increases the resonance frequency of resonator 101.

As shown in FIGS. 1 and 2, resonator 101 has a circular profile. In other embodiments, however, resonator 101 can have any other suitable shape. For example, resonator 101 can have a polygonal profile such as a triangular shape, a square shape, a rectangular shape, a pentagonal shape, a hexagonal shape, a heptagonal shape, or an octagonal shape. A major dimension $D_0$ in the x-direction or y-direction that is perpendicular to electronically conductive segment 102 can be represented as a diameter or width of resonator 101. The major dimension can be in a range of from about 5 mm to about 100 mm, about 15 mm to about 60 mm, or less than, equal to, or greater than about 5 mm, 10, 15, 20, 25, 30, 35, 40, 45, 50, 55, 60, 65, 70, 75, 80, 85, 90, 95, or about 100 mm.

A height or thickness, measured in the z-direction, of electronically conductive segment 102 can be set to any value. For example, a thickness of electronically conductive segment 102 can be in a range of from about 10 µm to about 100 µm, about 20 µm to about 40 µm, or less than, equal to, or greater than about 10 µm, 15, 20, 25, 30, 35, 40, 45, 50, 55, 60, 65, 70, 75, 80, 85, 90, 95, or about 100 µm. The thickness of electronically conductive segment 102 can affect the resonance frequency of resonator 101. Increasing the thickness of electronically conductive segment 102 too much, however, can result in resonator 101 being too thick for certain applications.

Polymeric component 104 is located between electronically conductive segment 102 and fluidic channel component 106. Polymeric component 104 coats a portion of the total surface area of electronically conductive segment 102. For example, polymeric component 104 coats from about 10 percent surface area to about 70 percent surface area of the electronically conductive segment 102, about 20 percent surface area to about 33 percent surface area, or less than, equal to, or greater than about 10 percent surface area, 15, 20, 25, 30, 35, 40, 45, 50, 55, 60, 65, or about 70 percent surface area. Polymeric component 104 can have a height or thickness in the z-direction that can be in a range of from about 10 µm to about 100 µm, about 20 µm to about 40 µm, or less than, equal to, or greater than about 10 µm, 15, 20, 25, 30, 35, 40, 45, 50, 55, 60, 65, 70, 75, 80, 85, 90, 95, or about 100 µm.

Polymeric component 104 can include an electronically insulating material. For example, polymeric component 104 can include a polyimide. Where present, the polyimide can include a repeating unit having the structure according to Formula I:

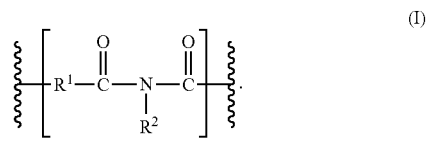

In Formula I, $R^1$ can be chosen from —O—, —NH—, and substituted or unsubstituted ($C_1$-$C_{20}$)hydrocarbylene. Additionally, $R^2$ can be chosen from —H, —OH, and substituted or unsubstituted ($C_1$-$C_{20}$)hydrocarbyl. In some embodiments the ($C_1$-$C_{20}$)hydrocarbylene can be chosen from ($C_1$-$C_{20}$)alkylene, ($C_1$-$C_{20}$)alkenylene, ($C_1$-$C_{20}$)cycloalkylene, and ($C_1$-$C_{20}$)arylene. Additionally, in some embodiments, the ($C_1$-$C_{20}$)hydrocarbyl can be chosen from ($C_1$-$C_{20}$)alkyl, ($C_1$-$C_{20}$)alkenyl, ($C_1$-$C_{20}$)alkynyl, ($C_1$-$C_{20}$)acyl, ($C_1$-$C_{20}$)cycloalkyl, ($C_1$-$C_{20}$)aryl, and ($C_1$-$C_{20}$)alkoxy. The specific structure of the polyimide will depend on whether it may be stable during screen printing or etching and whether the polyimide is sufficiently insulative so that the resonator does not short during operation. An example of a suitable polyimide includes a polyimide sold under the tradename KAPTON sold by DuPont of Wilmington Delaware.

The portion of electronically conductive segment 102 that is free of contact with polymeric component 104 can be coated with a dielectric layer. Where present, the dielectric layer can have a height or thickness in the z-direction that is equal to or greater than that of polymeric component 104. For example, the thickness can be in a range of from about 0.30 mm and about 2 mm, about 0.90 mm to about 1.1 mm, or less than, equal to, or greater than about 0.30 mm, 0.35, 0.40, 0.45, 0.50, 0.55, 0.60, 0.65, 0.70, 0.75, 0.80, 0.85, 0.90, 0.95, 1, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95 or about 2 mm. Additionally, a major dimension such as a width in the x-direction or y-direction can be the same as a width in the x-direction or y-direction as polymeric component 104. The dielectric layer can shield electronically conductive segment 102 and can include any suitable dielectric material. Examples of suitable dielectric materials include a bismaleimide-triazine (BT) resin, an epoxy resin, a polyurethane, a benzocyclobutene (BCB), a high-density polyethylene (HDPE), and combinations thereof. In some examples, the dielectric material can be air that can be located within a chamber enclosing the portion of electronically conductive segment 102 that is free of contact with polyimide coating 104.

Resonator system 100 includes fluidic channel component 106. Fluidic channel component 106 is joined to polymeric component 104 by an adhesive. The adhesive can be a pressure-sensitive adhesive or an acrylic adhesive. Fluidic channel component 106 is formed from a polydimethylsiloxane. However, in further examples, fluidic channel component 106 can be formed from other soft polymers such as a rubber or a hard polymer such as polyether ether ketone (PEEK). The polydimethylsiloxane can be subjected to a laser ablation process to form microfluidic channel 108 therein. Microfluidic channel 108 includes inlet 110 and vent 112. Microfluidic channel 108 is continuous and can have a shape that is generally commensurate with that of electronically conductive segment 102. However, it is possible for it to be shaped to conform to any suitable profile. Generally, vent 112 serves to help to force a liquid (e.g., perspiration) through microfluidic channel 108, but in some instances vent 112 can be configured as an outlet. In most examples, however, microfluidic channel 108 is configured to only hold a fixed amount liquid and will not allow that liquid to exit.

Figure 3:
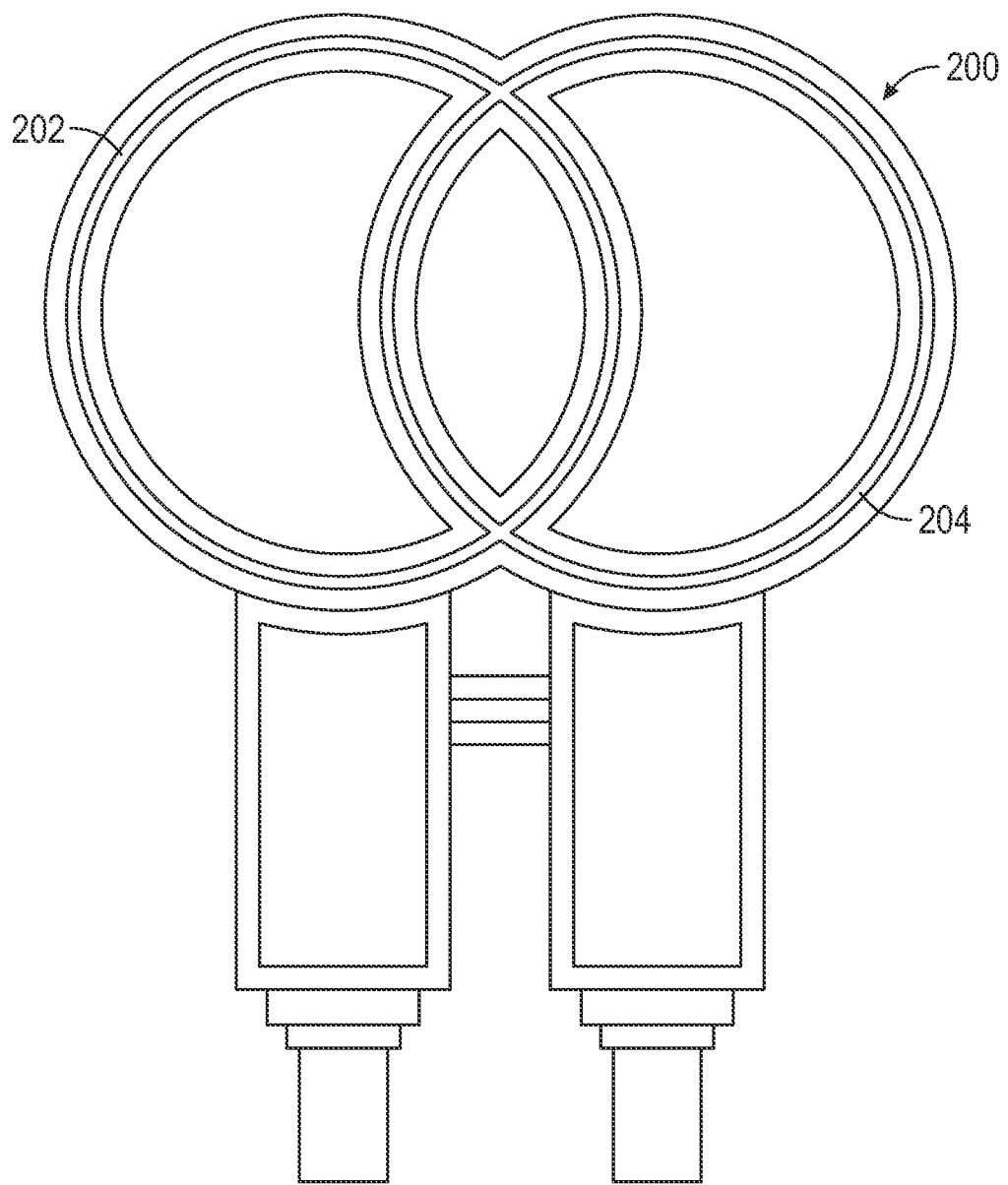
FIG. 3 is a plan view of a resonator reader.

Resonator system 100 can further include resonator reader 200. FIG. 3 is a plan view of resonator reader 200. As shown in FIG. 3 resonator reader 200 includes first electronically conductive loop 202 and second electronically conductive loop 204. Resonator reader 200 further includes first connector 206 and second connector 208. First electronically conductive loop 202 and second electronically conductive loop 206 can independently include an electronically conductive metal such as copper, silver, gold, aluminum, alloys thereof, or mixtures thereof. A diameter of each of loops 202 and 204 can independently range from about 5 mm to about 100 mm, about 15 mm to about 60 mm, or less than, equal to, or greater than about 5 mm, 10, 15, 20, 25, 30, 35, 40, 45, 50, 55, 60, 65, 70, 75, 80, 85, 90, 95, or about 100 mm. As shown in FIG. 3, loops 202 and 204 overlap. A distance between overlapping regions of reader 200 can be in a range of from about 5 mm to about 100 mm, about 15 mm to about 60 mm, or less than, equal to, or greater than about 5 mm, 10, 15, 20, 25, 30, 35, 40, 45, 50, 55, 60, 65, 70, 75, 80, 85, 90, or about 95.

Connectors 206 and 208 can connect resonator reader 200 to a component such as a vector network analyzer. The vector network analyzer can in turn be connected to a computer. The connection between the vector network analyzer and the computer can be through a wire or an antenna. Loops 202 and 204 as well as connectors 206 and 208 are at least partially enclosed by a dielectric material. Examples of suitable dielectric materials include a polyimide, a bismaleimide-triazine (BT) resin, an epoxy resin, a polyurethane, a benzocyclobutene (BCB), a high-density polyethylene (HDPE), and combinations thereof.

Resonator reader 200 can be positioned substantially in line with resonator 101. A distance between resonator reader 200 and resonator 101 can be varied to improve performance. For example, a distance between resonator reader 200 and resonator 101 can be in a range of from about 1 mm to about 10 cm. Resonator reader 200 can read the resonance frequency in resonator 101, through a variety of materials disposed therebetween. That is to say, resonator reader 200 and resonator 101 do not need empty space therebetween. For example, resonator reader 200 can wirelessly read the resonance frequency of resonator 101 through a polymeric material (e.g., polyphenyl ether) or a woven material.

Resonator system 100 is described as including one resonator 101 and one resonator reader 200. However, in further embodiments resonator system 100 can include any plural number of resonators 101 and readers 200. In embodiments that include multiple resonators, each resonator can be designed to have a different initial resonant frequency. This can be accomplished by varying any parameter such as respective lengths of electronically conductive segments 102 or altering pitches 110 and 112. In certain examples, it may be desirable to attach multiple resonator systems 100 at various locations on a user to monitor the amount of perspiration generated across the user's body.

Resonator system 100 can include an adhesive portion to allow resonator system 100 to be attached to a user. In some examples, resonator system 100 can be incorporated into a woven garment.

In operation, resonator system 100 detects the presence and amount of perspiration generated by a user while wearing resonator system 100. Moreover, resonator system 100 can detect the amount of an electrolyte of interest (e.g., sodium, potassium, or magnesium) present in the perspiration. Detecting perspiration using resonator system 100 includes measuring a first resonance frequency of resonator 101. The first resonance frequency is the resonance frequency of resonator 101 before perspiration enters microfluidic channel 108. When the perspiration enters microfluidic channel 108 the electrical environment around electronically conductive segment 102 changes. The changing electrical environment causes the resonance frequency of resonator 101 to change. Thus, if a second resonance frequency of resonator 101 is measured that is different than the first resonance frequency the presence of the of perspiration can be confirmed. By measuring the rate of change of the resonance frequency it is possible to monitor the rate of the perspiration that is generated. At least one of the first resonance frequency and the second resonance frequency can be in a range of from about 1 MHz to about 500 MHz, about 1 MHz to about 100 MHz, or less than, equal to, or greater than about 1 MHz, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or about 500 MHz. Additionally, the amplitude of the resonant frequency signals generated can allow for the determination of the amount of electrolyte that is generated. A larger peak height indicates a higher electrolyte e.g., salt) concentration in the perspiration.

Resonator system 100 can be deployed in many different mediums to detect perspiration. For example, resonator system 100 can be used by athletes, firefighters, military personal, or other people whose jobs or activities result in perspiration levels that should be monitored.

Resonator system 100 can be assembled according to any suitable method. For example, an assembly including any of the electronically conductive metals described herein coated to the material of the polymeric component can be etched to form the pattern (e.g., the spiral) of electronically conductive segment 102. To form the pattern the electronically conductive metal can have the pattern printed on the surface to effectively block some portions of the electronically conductive metal from the etchant. The pattern can be printed with an indelible marker.

Etching can include at least partially immersing the electronically conductive segment in a solution comprising an etchant. The etchant can include any solution capable of etching the electronically conductive metal but not the polymeric component. As an example, the etchant can include hydrogen peroxide and hydrochloric acid.

Following etching the substrate is contacted with polymeric component 104. A precursor to fluidic channel component 106 is adhered to polymeric component 104. The precursor is exposed to a laser to ablate the precursor to begin to form microfluidic channels 108. Microfluidic channels 108 are finally formed by plasma sealing.

EXAMPLES

Various embodiments of the present disclosure can be better understood by reference to the following Examples, which are offered by way of illustration. The present disclosure is not limited to the Examples given herein.

Example 1

Sweat loss can help determine: hydration status of individuals working in harsh conditions, which is especially relevant to those who wear thick personal protective equipment (PPE) such as firefighters. A wireless, passive, conformable sweat sensor sticker is described here that can be worn under and interrogated through thick clothing to simultaneously measure sweat loss volume and conductivity. The sticker includes a laser-ablated, microfluidic channel and a resonant sensor transducer. The resonant sensor is wirelessly read with a handheld vector network analyzer coupled to two, co-planar, interrogation antennas that measure the transmission loss. A sweat proxy is used to fill the channels and it is determined that the sensor can orthogonally determine the sweat conductivity and volume filled in the channel via peak transmission loss magnitude and frequency respectively. A four-person study is then used to determine level of sensor variance caused by local tissue dielectric heterogeneity and sensor-reader orientation.

Sweat is rich in biomarkers with clinical relevance and can be sampled non-invasively. There is also a putative link between sweat sodium (Na+), potassium (K+), and chloride (Cl−) levels and sweat rate and hydration status. Besides biomarkers, sweat rate, total loss, and local sweat loss have potential uses for monitoring hydration status. Monitoring sweat loss specifically finds applications in sports performance monitoring and general health monitoring. This can be especially beneficial for individuals working in harsh environments such as construction workers working in hot, humid climates or firefighters in structural fires. Firefighters, in particular, are at a high risk of dehydration. Studies have shown that due to the harsh conditions in a structural fire even ad libitum drinking may be insufficient to properly rehydrate. Devices that could detect on body measurement of sweat loss could help prevent serious health complications from dehydration in firefighters and help EMT personnel know if additional measures should take place beyond intake of fluids for proper rehydration. However, potential issues with measuring changes in body mass are 1) hidden water mass absorbed into clothing and 2) pooled sweat on the skin surface. Other considerations to factor are the effects of fitness level, body type, and heat acclimation on sweat rates. Also, variation in sweating rates between individuals and regions of the body need to be accounted for in any sweat loss analysis with some possible correlations between regions. To realize robust sweat monitoring, tailored sensors capable of multi-region monitoring are needed. Low-cost sweat rate and sweat composition sensors need to be developed, especially ones that can be worn comfortably below PPE.

Sweat sensors already presented in the literature can be classified by two distinct features: sweat sampling method and interrogation method. Example sample handling strategies include use of microfluidics, wicking materials, and natural ventilation strategies. The most accurate method is natural ventilation as it can detect both sensible (liquid) and insensible (vapor) sweat loss, but wearable implementation can prove to be difficult and bulky particularly under personal protective equipment (PPE). Wicking materials and microfluidics are simpler for wearable implementation with microfluidics having the advantage for reusable sensors whereas wicking materials are usually single-use devices. Transduction methods include potentiometry, capacitance, optical, and impedance. These transduction methods have been implemented with great success thanks to miniaturized electronics and ability to wireless interrogate signals via Wi-Fi, Bluetooth, and near field connections. Even with the recent advances in sweat sensor development one application that proves difficult to implement is undercoat perspiration. This is due to either the transduction method requiring a direct line of sight (e.g. optical), or bulky sensor implementation with multiple powered parts and integrated circuit boards. These become especially problematic for applications where the user is already encumbered with bulky gear and thick PPE, such as firefighters.

One sensor type that could decrease the size of wireless sweat rate sensors for applications through thick PPE is resonant sensors. As their name denotes, these are simple circuits that resonate at a specific frequency dependent on their effective inductance and capacitance. Changes in permittivity of the surrounding medium can affect the latter parameter, and thus shift the resonant frequency. Wireless resonant sensors have been used for several biomedical applications in the past including intraocular, wireless power transfer for implanted sensor, and vital signs. This class of sensors has also been demonstrated to monitor biofluids for monitoring of proteins and also have the potential to characterize tissue dielectric properties and enzyme activity. Resonant sensors have the potential to be a simple solution to sweat analysis.

Figure 4A:
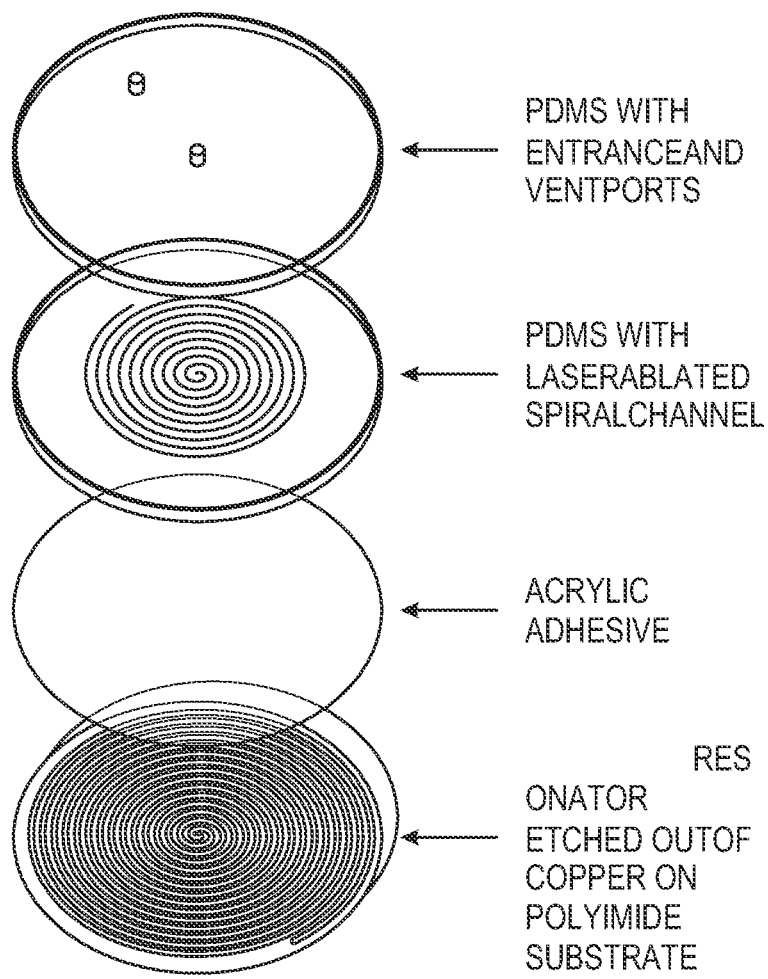
FIG. 4A is an exploded view of a resonator system.
Figure 4B:
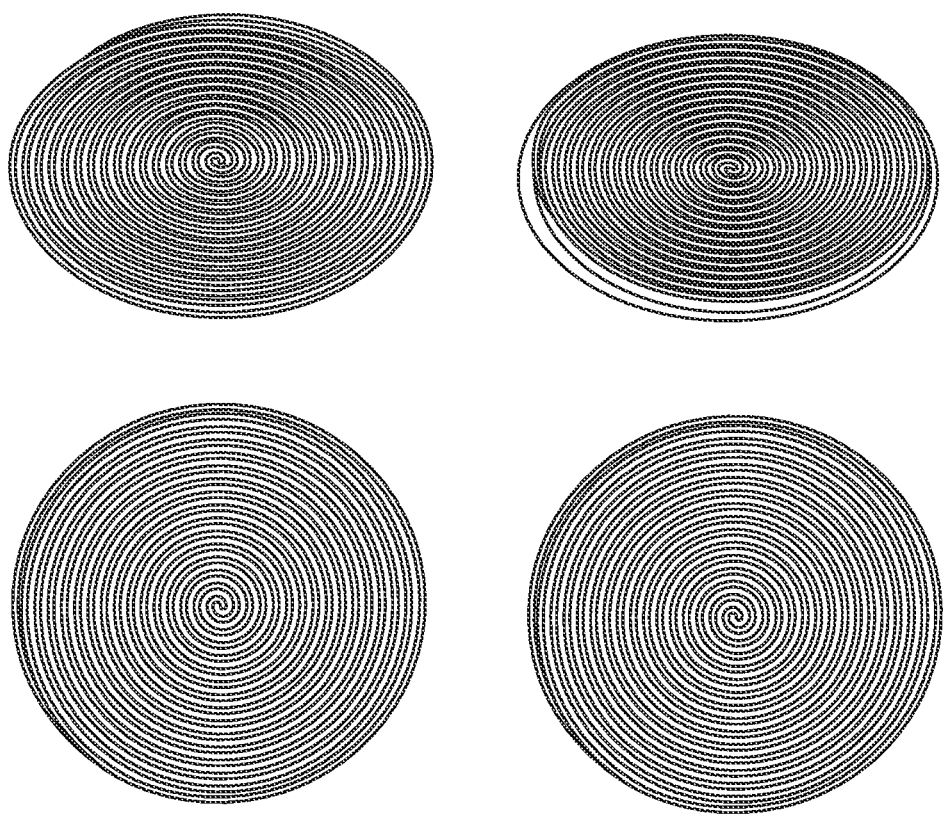
FIG. 4B shows two perspective views as well as a top and bottom view of the resonator system
Figure 5A:
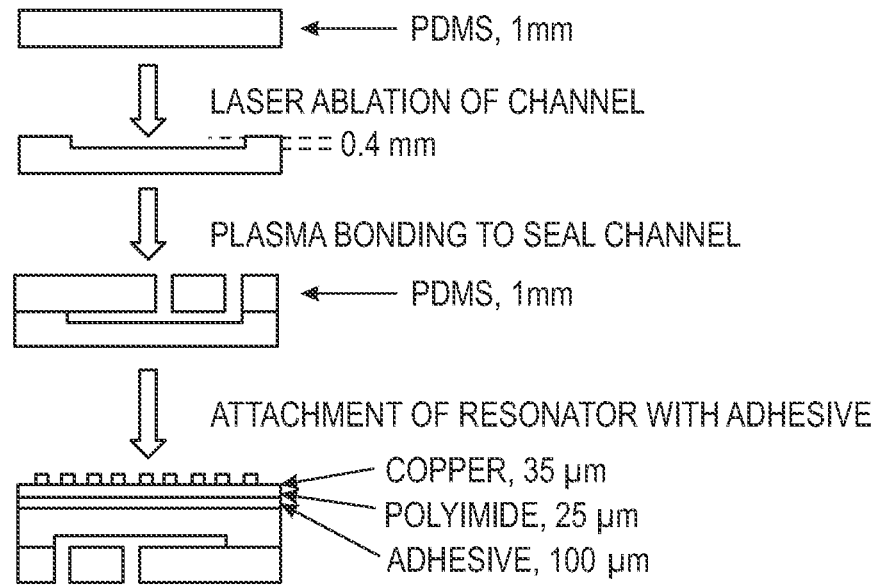
FIG. 5A is a schematic view showing an assembly scheme of the resonator assembly and data obtained therefrom.
Figure 5B:
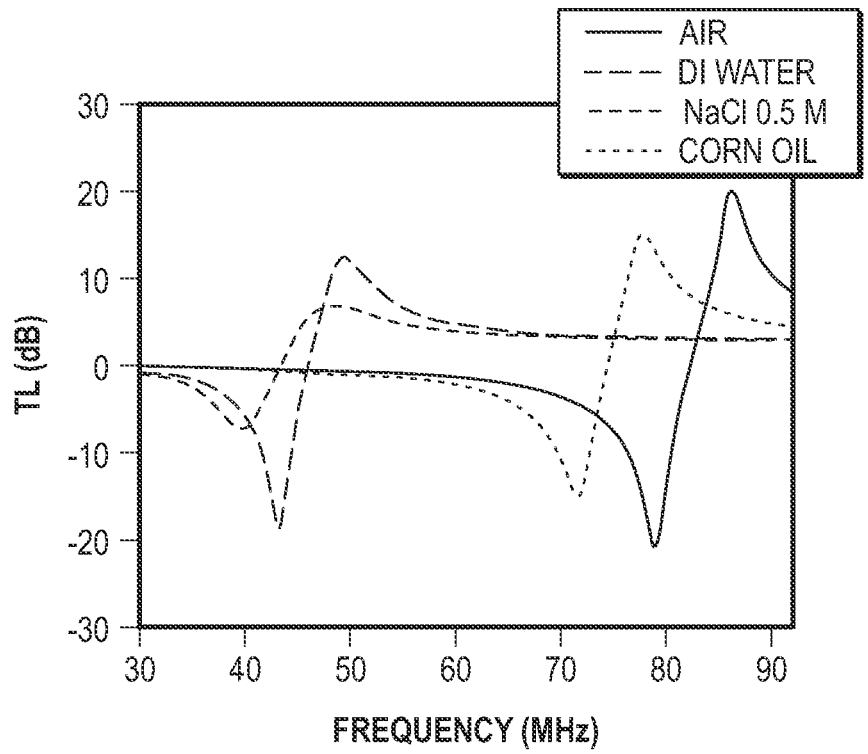
FIG. 5B is a graph showing data obtained from the resonator system with respect to changes in amplitude and peak frequency.
Figure 5C:
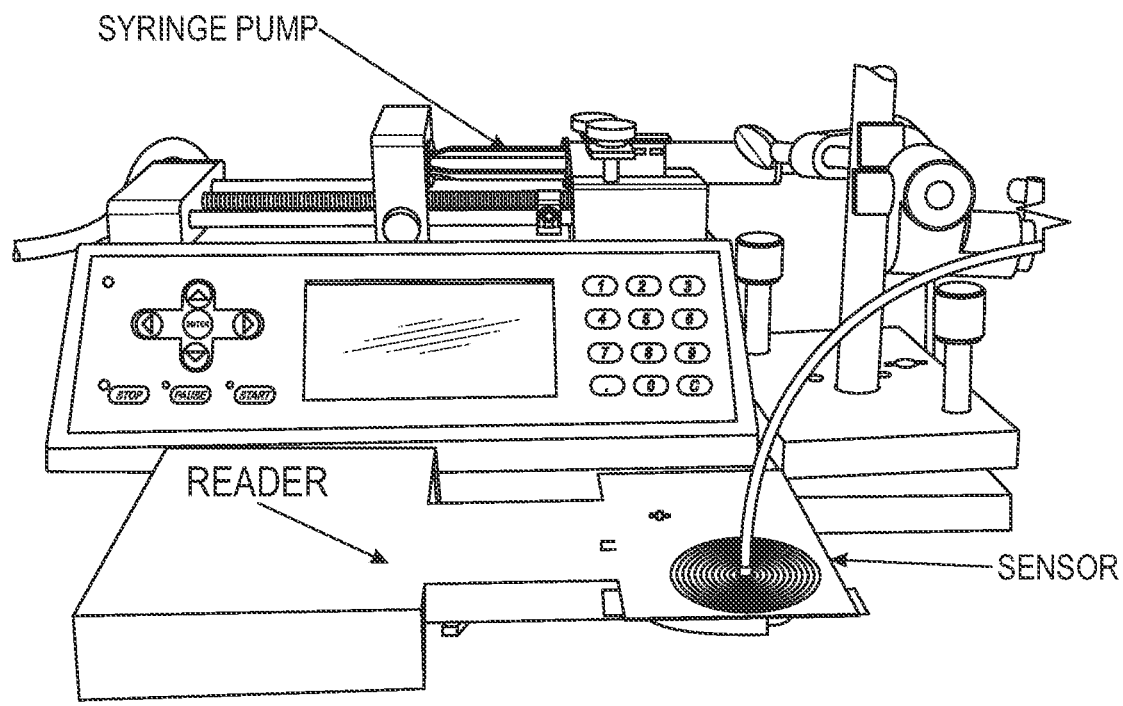
FIG. 5C is a schematic view of a custom reader for the resonator system.
Figure 5D:
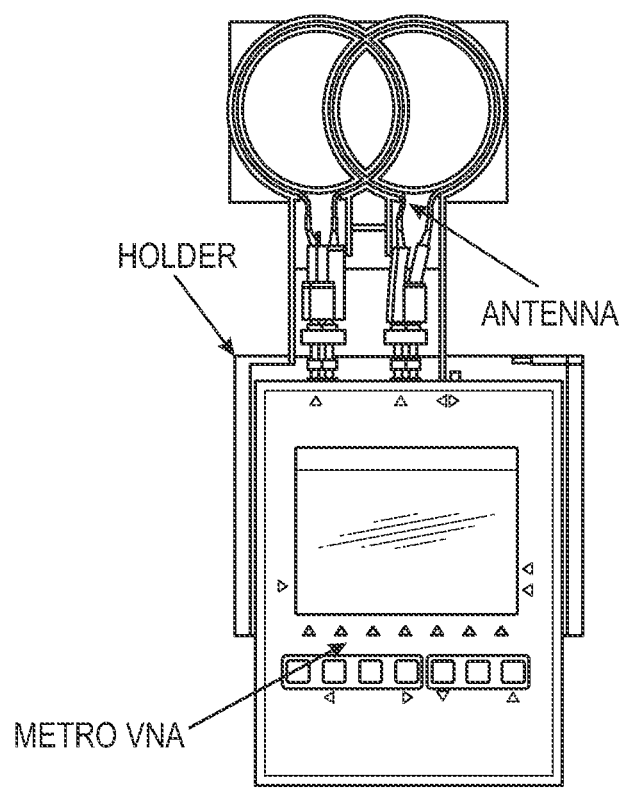
FIG. 5D is a vector network analyzer used to obtain signals from the resonator.

This Example provides the fabrication of a resonant sticker that can analyze sweat rate and sweat conductivity, which correlates to overall ion concentration. The sticker sensor is composed of fluid handling channels (PDMS) with an adhered resonator (FIG. 4). The resonator is in the shape of an Archimedean spiral, and is chemically etched out of a copper coated polyimide substrate (DuPont Pyralux) with an indelible marker mask. The channels are also in the shape of an Archimedean spiral and fabricated in polydimethylsiloxane (PDMS) using a craft laser cutter and sealed using a separate piece of PDMS by plasma bonding (FIG. 5a). An Archimedean spiral was chosen for the geometry of the resonator as it works well for inductively coupled sensing systems, is simple to fabricate. The VNA analyzes the transmission loss (TL) of the reader antenna/resonator system which changes in amplitude and peak frequency ($f_o$) and is determined by the complex permittivity of the surrounding medium (FIG. 5b). For this study, the sweat sensor sticker was analyzed both on the reader and through thick firefighter PPE (Morning Pride TAILS) to calibrate the sensor response and determine ability to read through clothing. The sensor was analyzed using the custom reader and filled using a syringe pump (FIG. 5c). The custom reader was fabricated out of a low-cost, portable vector network analyzer (VNA, MetroVNA) and fitted into a custom holder with a double coil antenna (FIG. 5d) used to interrogate the sweat sticker via inductive coupling between a reader antenna and resonant sensor. The Example also measured the sensor on a small cohort of human subjects to determine sources of variability that the Example will need to control before attempting a larger human trial. Finally, the Example addresses the current limitations and detail next steps to enable resonant sensors for sweat analysis.

The sweat analysis sticker developed for this study is composed of microfluidic channels to distribute the sample across the resonator which can then wirelessly and rapidly transduce local sweat loss and sweat conductivity.

Microfluidics are most frequently fabricated using photo- and soft lithographic methods which utilize a master mold to fabricate microchannels and structures in elastomeric materials. This technique is good for rapid replication of a single microfluidic design, but can become cumbersome during the prototyping stage where a new master mold has to be made for every design change. Another method to rapidly fabricate microfluidic devices is laser ablation of polymer blocks. Although the literature has reported laser ablation of PDMS to make channels, the Example was not able to find a convenient model to describe how the depth and width of channels in PDMS are controlled by the power and duration of a stock $CO_2$ laser cutter. Applying a similar approach found in literature and with the aid of a 3D digital microscope, the Example developed a model for laser ablated channel dimension. Eighty-eight straight channels were ablated into pre-cured sheets of PDMS and the resulting dimensions were determined using an Olympus DSX110 digital microscope.

The depth model, fit to the analyzed data, was derived from a mass balance where the mass flux, m" is a function of the heat flux from the laser, Q", and the heat of pyrolysis of the material, L, $$m''=(Q''-Q''_o)/L \quad (1)$$

where $Q''_o$, represents the critical heat flux when pyrolysis of material will begin. The heat flux from the laser, Q" can be represented as $$Q''=\alpha\varphi_o \Delta t \quad (2)$$

where $\alpha$ is the absorptance of the material, $\varphi_o$ is the laser power, and $\Delta t$ is the irradiance time which is a function of half the laser length of the Gaussian beam width, a, and the cutting speed, v, $\Delta t=a/v$. Specifying the ablated area to be $\pi a^2$ and the density of PDMS ($\rho$), the depth (D) of the channel can then be determined as, $$c_1 = \frac{\alpha}{\rho \pi L a} \text{ and } c_2 = \frac{Q''_o}{\rho \pi L a^2}.$$

With constants $$D = \frac{c_1 \varphi_o}{v} - c_2 \quad (3)$$

Channels were ablated in PDMS using laser power settings between 8-24 W and cutting speed between 0.008-0.04 m/s using a low-cost, craft laser cutter in vector mode (GlowForge Plus). Resulting channel depth data were fit by the depth model (Eq. 3) and resulting model parameters of $c_1$=0.5357 (±0.063 at 95% confidence interval) μm/(J/m) and $c_2$=18.5 (±45.1)μm with coefficient of determination $R^2$=0.943 and RMSE=45.10 μm. A likely reason for the large RMSE value is the difficulty to cure PDMS to a uniform height. Even a small difference of 50 microns in height would have an effect on the focal point of the laser above the substrate which would create larger than expected channels in some cases. On the other hand, the model showed that the laser ablation technique is adequate for channels with an aspect ratio greater than 1.4 (minimum channel height of 100 μm with average width of 140 μm) which can accommodate volumes of sweat>14 μL, assuming a channel length of 1 m.

The width of the channels is a strong function of the laser beam diameter and remains relatively constant for different laser powers and cutting speeds. Upon inspection it was determined there is a linear correlation between channel width and channel depth (Eq. 4):

$$W=0.073D+110 \quad (4)$$

where W is the width of the channel and RMSE of the model is 17 μm; with a correlation coefficient of 0.635. Although the effect of laser power and cutting speed on the channel widths and depths from the craft laser cutter has relatively large variation they were found suitable for design of devices in this study for sweat storage and handling. A major benefit of using laser ablation over other soft lithography or SLA printing is the ability to rapidly prototype designs. This can be useful in designing different size channels to accommodate individuals with lower or higher sweating rates. Laser cutting PDMS coupled with plasma bonding results in a process which can go from conceptual design to prototype in a short amount of time. As an example four designs were created and tested within 15 minutes in the lab.

Sweat is a rich milieu of electrolytes, metabolites, and amino acids; however the dominant component for each person is sodium chloride (NaCl) making up most of the charge carriers in sweat and thus mostly responsible for sweat conductivity. Although the conductivity of sweat is not an established clinical method to monitor hydration studies have demonstrated correlation between hydration level and sweat conductivity. Because of the relatively large amount of NaCl present in sweat, simple solutions of NaCl have been used to mimic the conductivity of human sweat, rather than reconstituting all lower concentration contributors. The Example used similar sweat proxy solutions to test the response of the flexible resonant sensor stickers, detecting changes in resonant frequency ($f_o$) and relative power transmission loss (TL) to increased conductivity, e.g. NaCl concentration from 0.01-0.1 mol/L.

Figure 6B:
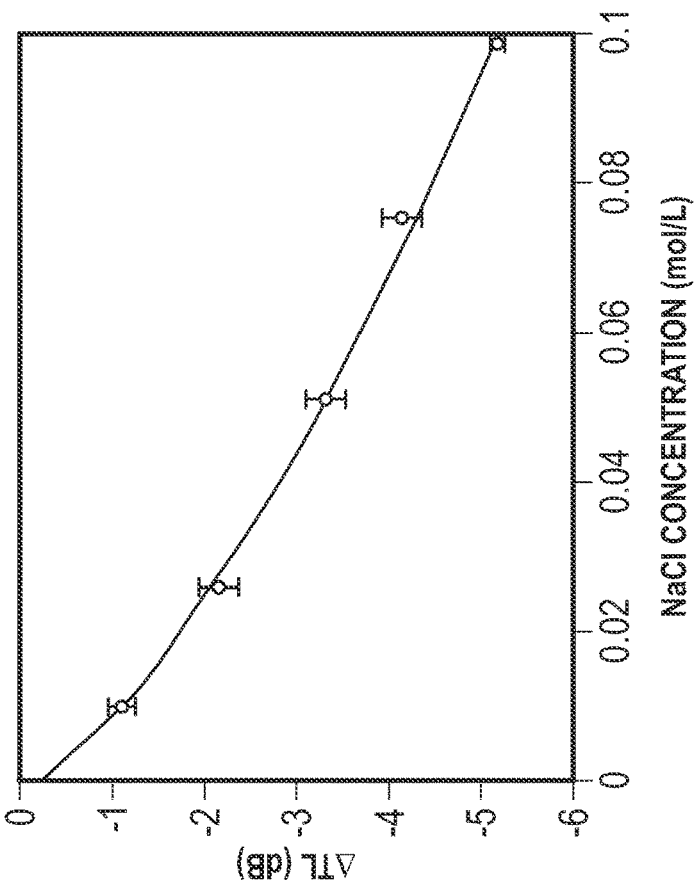
FIG. 6B is a graph showing data obtained using the resonator system.
Figure 6A:
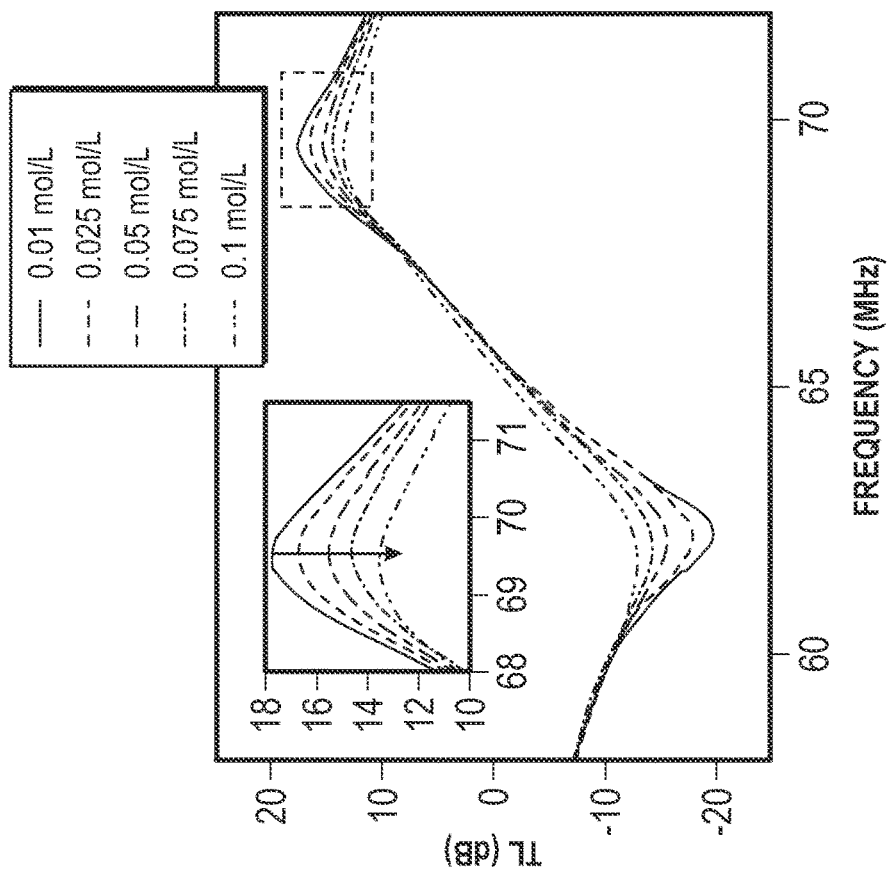
FIG. 6A is a graph showing data obtained using the resonator system.

From the TL data it is observed that the amplitude of the resonant peak decreases as the conductivity increases meaning that the losses decrease with increasing concentration (FIG. 6a). This is apparently in contrast with other reports which show that losses increase with concentration due to the decrease in permittivity and increase in conductivity. A possible explanation, without intending to be bound by any theory, for this is that the microfluidic chip with filling solution is acting as a matching network for the resonator and reader antenna system. As the salt solution is increasing it is matching the impedance of the resonator to the reader antenna leading to a more lossless power transfer. A similar phenomena was recently observed in a study conducted in the lab characterizing solvated ions using resonator arrays.

Figure 6D:
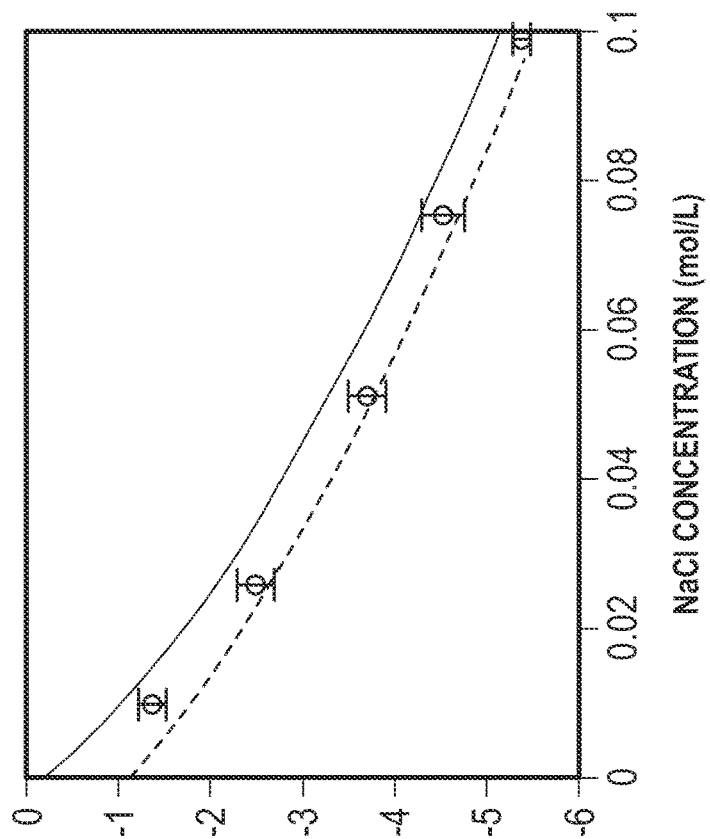
FIG. 6D is a graph showing data Obtained using the resonator system.
Figure 6C:
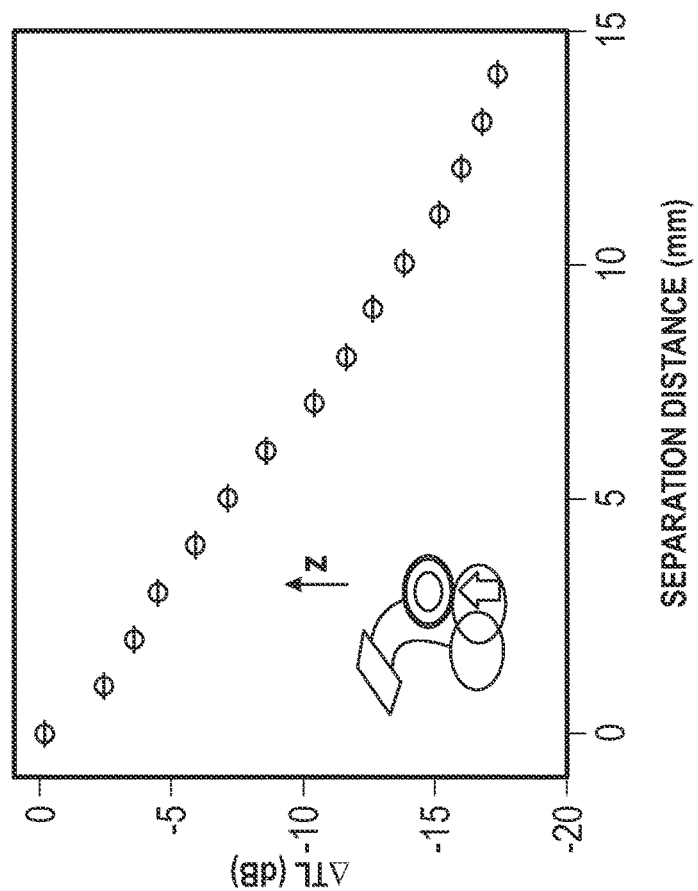
FIG. 6C is a graph showing data obtained using the resonator system.

The change in TL ($\Delta$TL) was calculated from the zero concentration solution and a quadratic model was fit to the data of the form $$\Delta TL = p_1 \sigma^2 + p_2 \sigma \quad (5)$$

with $R^2$ of 0.964 with $p_1$=0.19 and $p_2$=−1.08 (FIG. 6b). NaCl solutions were then tested in the sensor while reading through the thick PPE to determine the efficacy of the model to predict conductivity through the material. There was a consistent offset between the model and the PPE data which is purported to be a result of displacement between the reader antenna and the resonator due to the thickness of the PPE. In order to correct for this offset, the effect of separation distance on $\Delta$TL was determined (FIG. 6c), which fit a linear model with a slope of 1.345 $\Delta$TL/mm. With the PPE thickness being 0.9 mm the offset was calculated as −1.2 once this correction factor was added to the model the Example showed a better prediction of conductivity through PPE for conductivities about 0.01 mol/L which is the starting point for range of sweat conductivity (FIG. 6d).

The effect of sweat volume (distance filled in the sensor channel) on resonant response was also determined. The distance filled has a significant effect on the change in $f_o$ ($\Delta f_o$, FIG. 7a). It was hypothesized that as the channel fills with sweat, the resonant frequency will shift down as the relative permittivity of water is ~80 times greater than that of air, thus increasing the capacitance in the channel as capacitance is directly proportional to relative permittivity.

This inverse relationship of capacitance and resonant frequency is described by the fundamental equation for resonant frequency, $$f_o = \frac{1}{2\pi\sqrt{LC}} \quad (6)$$

where L is the inductance and C is the capacitance.

Figures 7A, 7B:
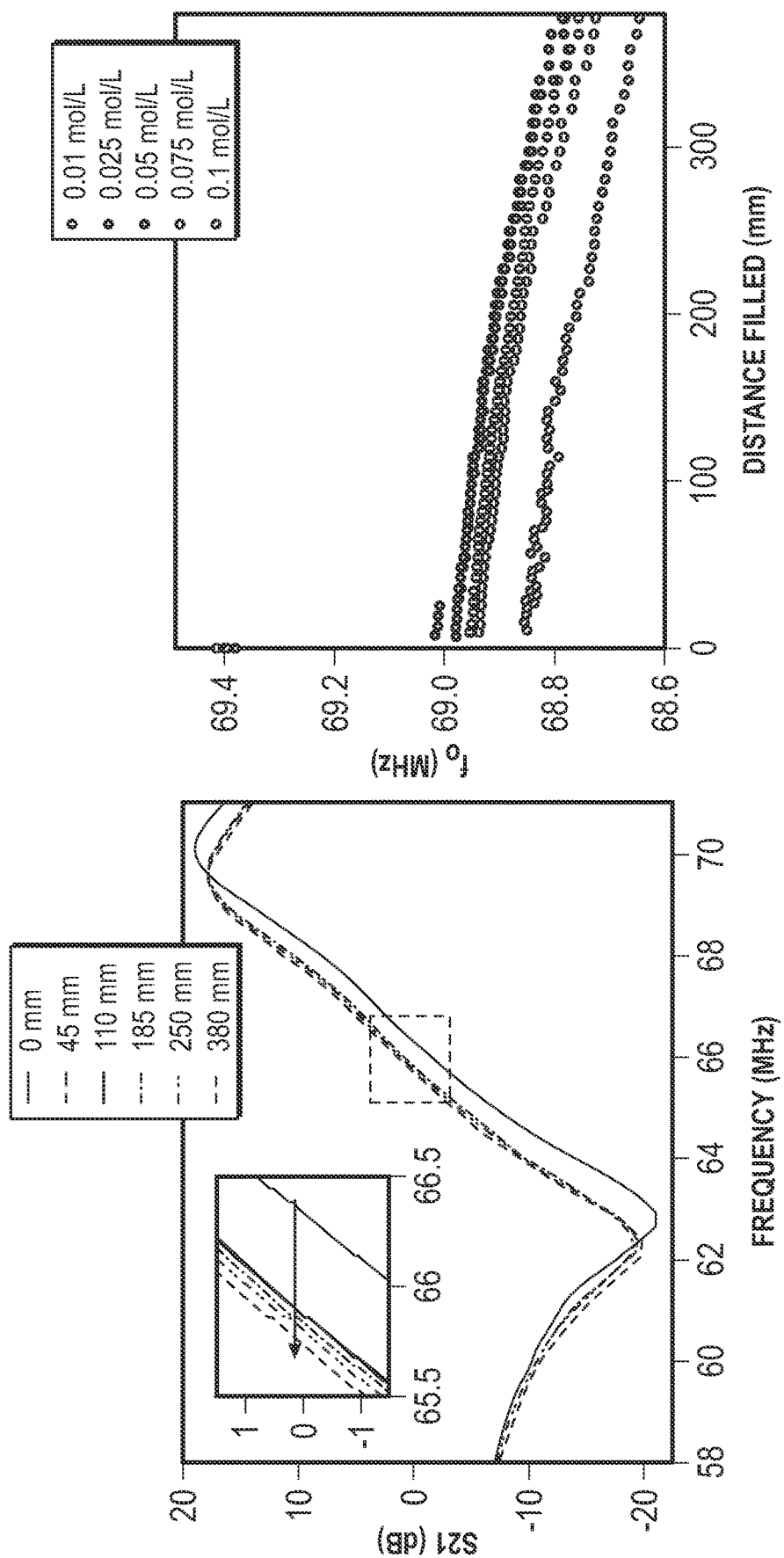
FIG. 7A is a graph showing data obtained using the resonator system.
FIG. 7B is a graph showing data obtained using the resonator system.
Figure 7D:
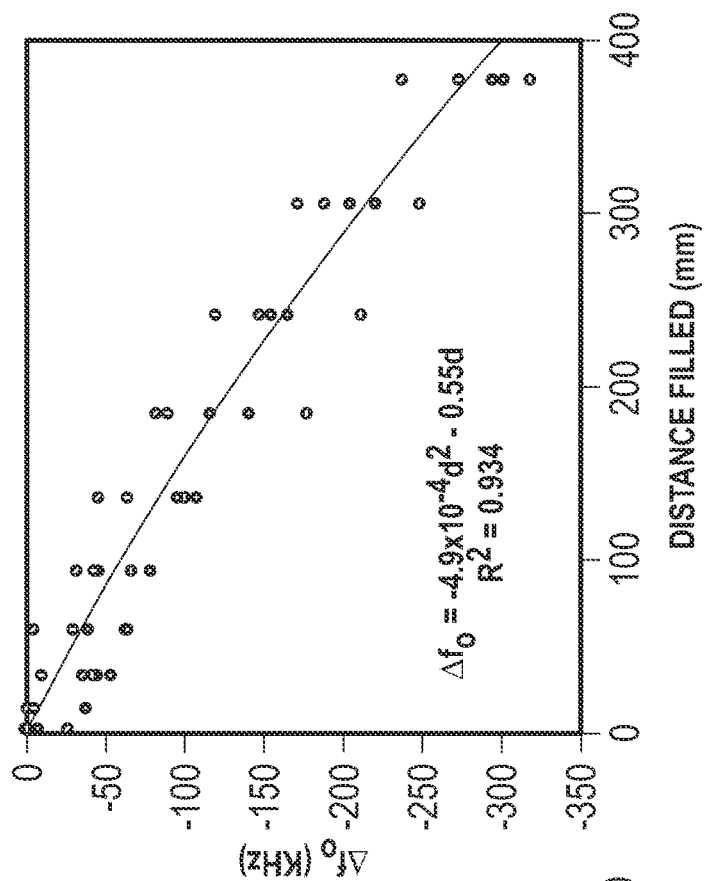
FIG. 7D is a graph showing data obtained using the resonator system.

When initially filling the channels (going from air to small amount of fluid) the Example observed a relatively large, initial step decrease in resonant frequency (FIG. 7b). After this initial step change a more gradual, parabolic decrease is observed upon addition of more fluid. For these experiments $\Delta f_o$ was calculated by normalizing to the first data point with fluid. The model for both the resonator on the reader and through PPE had the form of $$\Delta f_o p_1 d^2 + p_2 d \quad (7)$$

where $p_1$ and $p_2$ are constants and d is the distance filled in the channel. For the resonator directly on the reader $p_1 = -7.2 \times 10^{-4}$ kHz/mm$^2$ and $p_2 = -0.27$ kHz/mm with $R^2$ of 0.754 whereas for the resonator through PPE $p_1 = -4.9 \times 10^{-4}$ kHz/mm$^2$ and $p_2 = -0.55$ kHz/mm and $R^2$ of 0.934.

The quadratic response can be attributed to the fact that the sensor is observed to be more sensitive to dielectric changes towards the edge of the spiral than in the center. As the sensor is initially filled from the center, the sensor gain is not as steep as when the sensor is filled towards the outer edge, thus resulting in a quadratic transfer function. This phenomena can also be explained by the fact that the inner turns of a planar spiral resonator contribute less positive mutual inductance between the resonator and reader antenna and thus show a lower frequency response than that outer turns.

Figure 7C:
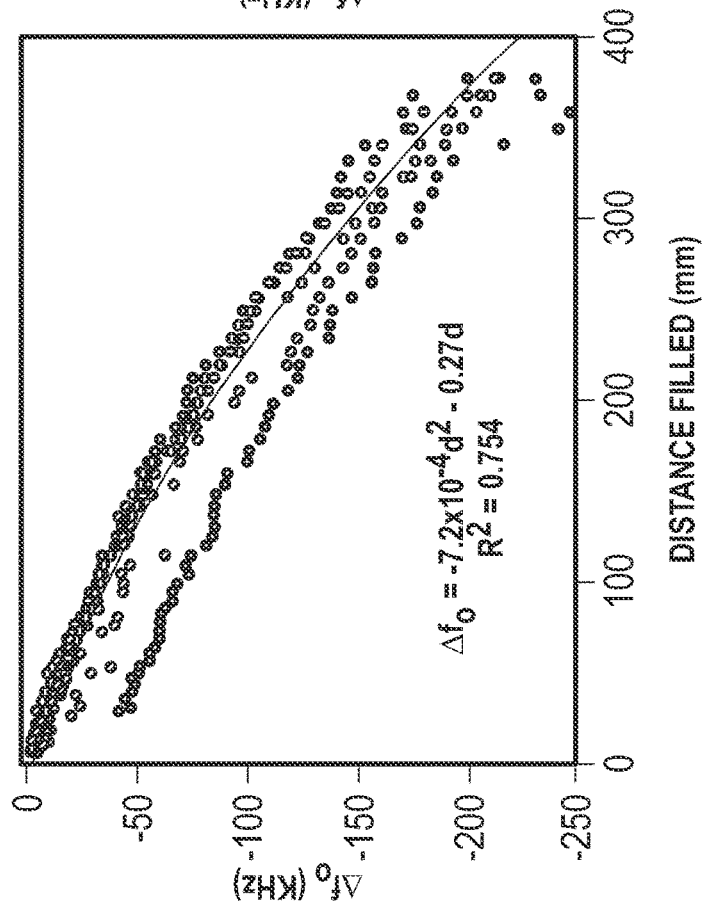
FIG. 7C is a graph showing data obtained using the resonator system.

Data sets for filling of the sensor either read directly on the reader and through the PPE both showed a quadratic response (FIGS. 7c,d) although the PPE data shows a faster changing slope than that taken directly on the reader. This would mean that a calibration curve for sweat rate should be generated for different types of PPE. However, since the response is quadratic a simple three to four-point calibration would be sufficient. Also, if larger volume channels were used to accommodate a higher local sweat rate then the increase in fluid volume would decrease the resonant frequency even further with distance filled. It is important to also note that the effect of filling fluid on the $\Delta$TL response for conductivity of the solution was found to be insignificant. This is a significant finding for this simple sensor architecture as it indicates that conductivity and sweat volume can be measured orthogonally using the same resonator sticker without the need for a multiplexed sensing system.

The effect of bending on the channel cross sectional area and high frequency stress cycles on the sensors response were tested. The cross sectional area did not appreciably change with bending meaning that the curvature of the body will have little effect on sensor performance. Cycle fatigue testing was also performed to determine the effect of repeated elastic deformation on sensor performance. From these tests it was determined that the sensor response remained stable even after 2000 cycles.

A goal for these sensors is to be deployed as inexpensive, single use stickers for measuring personal sweat rate and sweat composition. The fabrication of these sensors (etched or screen printed) make for an inexpensive wireless solution compared to other wireless transducers that involve more complex PCB boards, integrated circuits, and assembly. However, a few drawbacks to these simple resonators are their sensitivity to any dielectric material within $\neq 1.5$ cm proximity (which also affect the fringing fields) as well as sensitivity to position and orientation between reader and sensor which affects the sensor response.

Figure 8B:
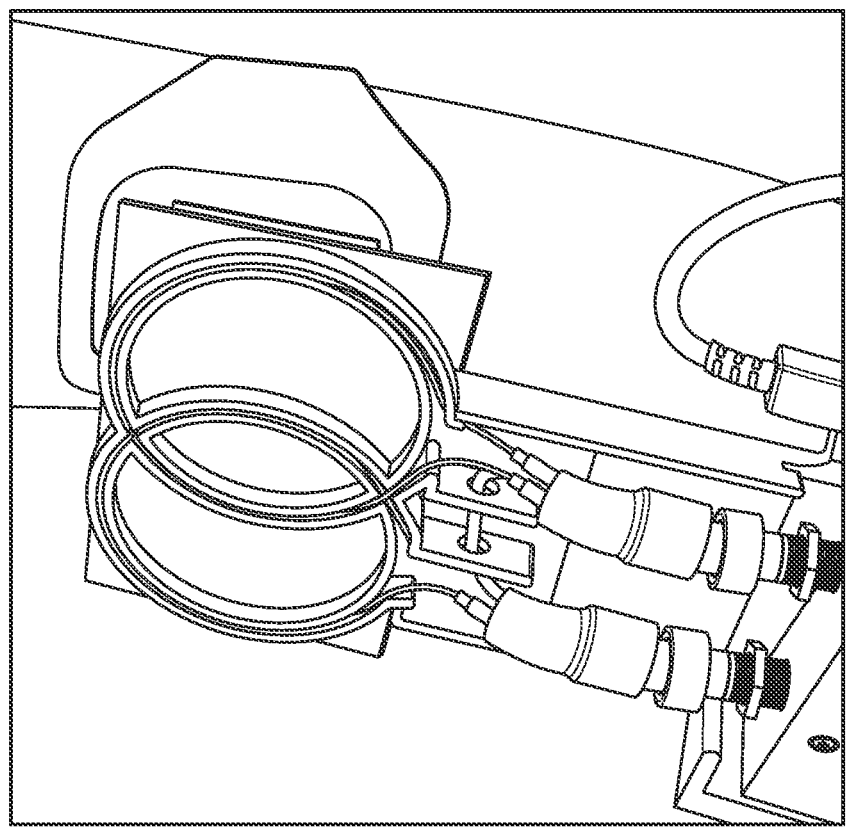
FIG. 8B shows a resonator reader disposed over the resonator.
Figure 8A:
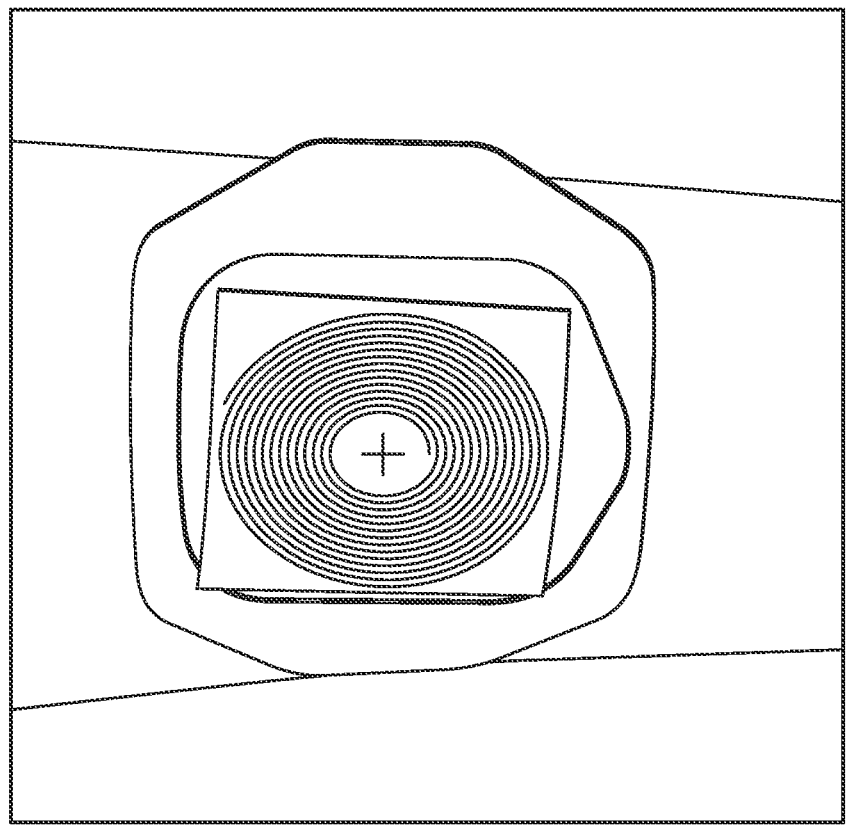
FIG. 8A shows a resonator system as a patch.
Figure 8C:
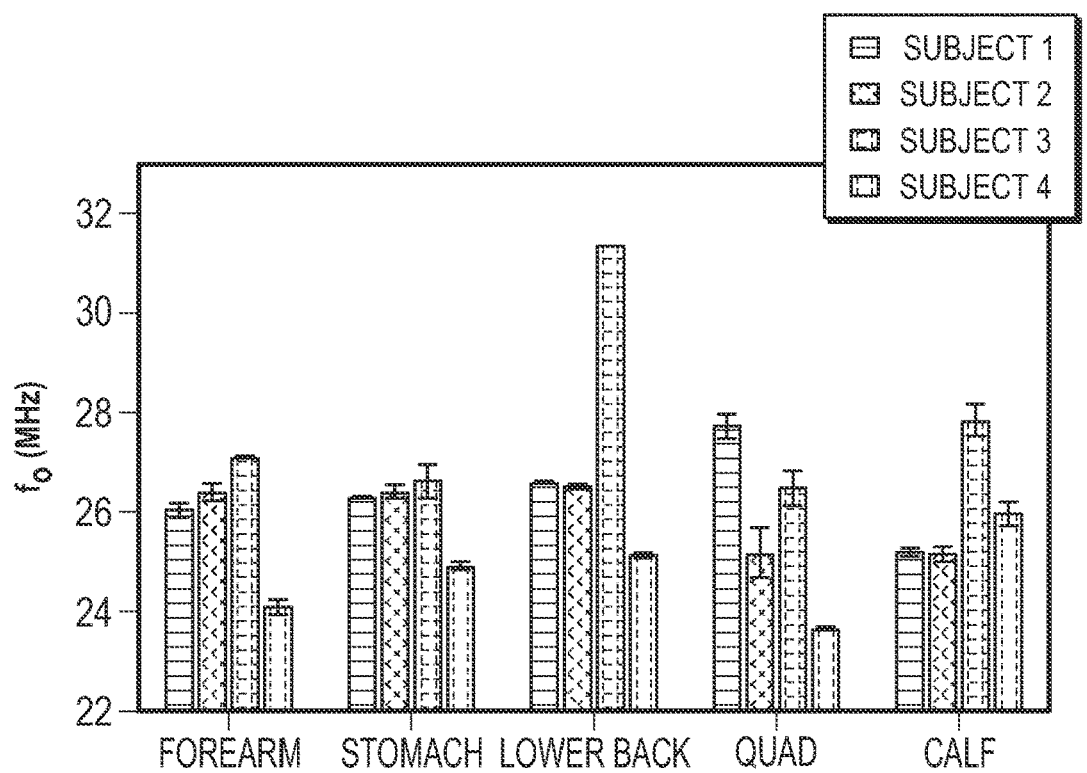
FIG. 8C is a graph showing data obtained using the resonator system.
Figure 8D:
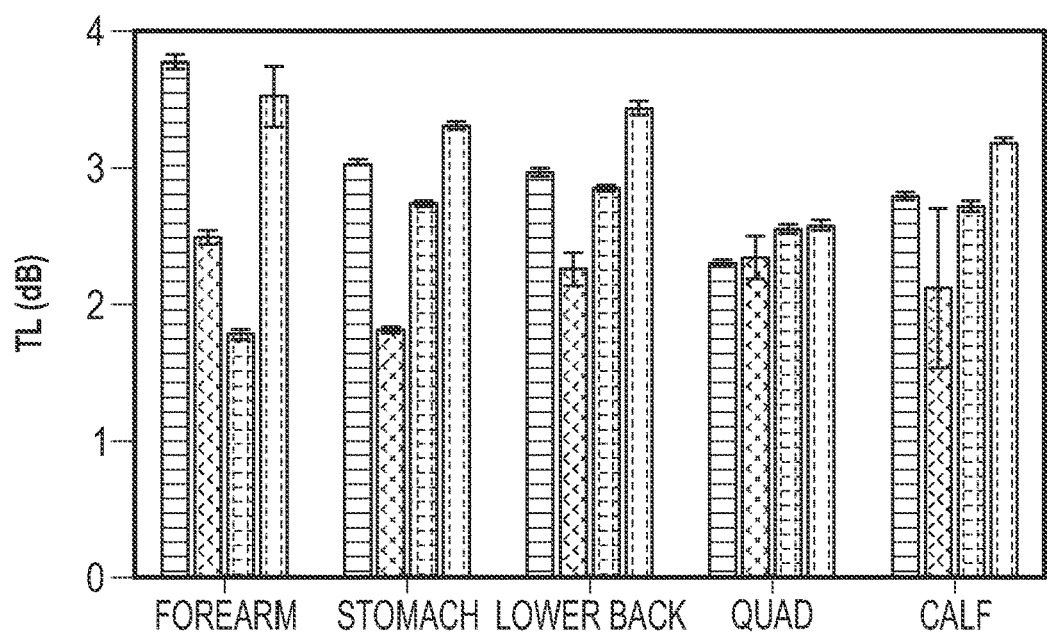
FIG. 8D is a graph showing data Obtained using the resonator system.
Figure 8E:
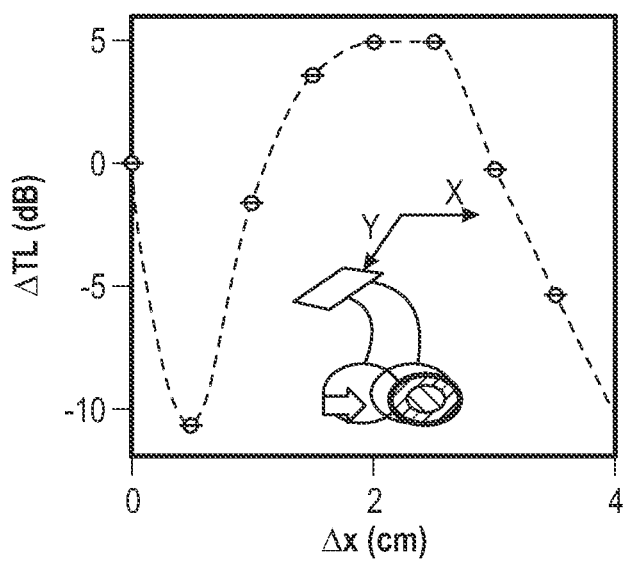
FIG. 8E is a graph showing data obtained using the resonator system.
Figure 8F:
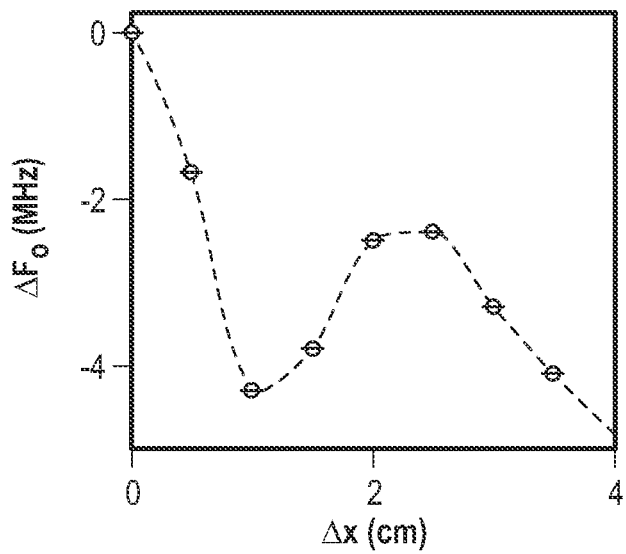
FIG. 8F is a graph showing data obtained using the resonator system.
Figure 8G:
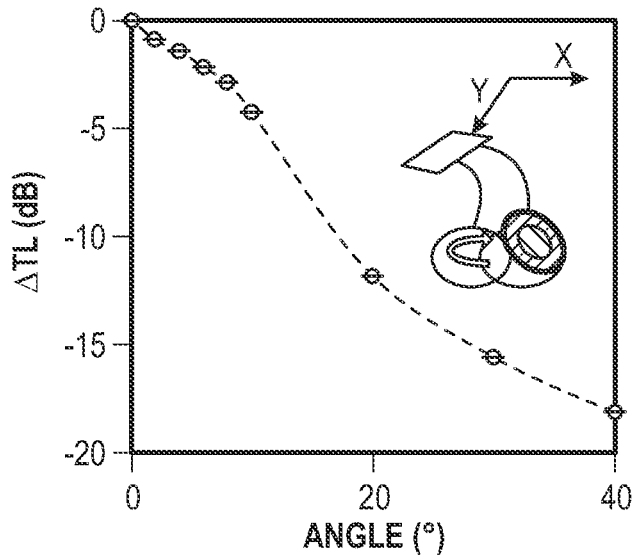
FIG. 8G is a graph showing data obtained using the resonator system.
Figure 8H:
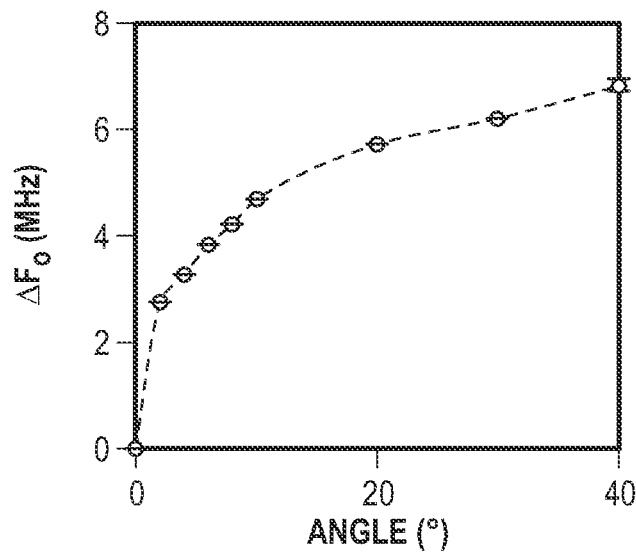
FIG. 8H is a graph showing data Obtained using the resonator system.

To prepare the sweat sensors for a larger-scale human trial, the Example first conducted an initial feasibility study with the resonators on a smaller cohort of human subjects to determine what level of sensor variance can be expected from these two confounding factors (local dielectric changes and sensor-reader orientation) (FIGS. 8a and 8b). These studies investigated both inter- and intra-human variation in TL responses with four male subjects being tested on 4 different areas of the body (forearm, stomach, lower back, thigh, and calf—FIGS. 8c, d). Each body part was scanned five times with the reader replaced on top of the patch each time to account for repositioning effect. The average standard error for $f_o$ and TL was 156 kHz and 0.08 dB respectively. Given the dynamic range for $\Delta$TL (6 dB) and $\Delta f_o$ (300 kHz) this would mean an expected signal to noise ratio of 75 for $\Delta$TL magnitude and 1.92 for $\Delta f_o$. A high signal to noise ratio (>3) for TL magnitude indicates sweat conductance is not impaired by spatial variation between reader and resonator. However for sweat rate, the reader sweat sticker orientation creates enough variation in the resonant frequency that it will prove difficult for analysis unless further mitigated.

Figure 8I:
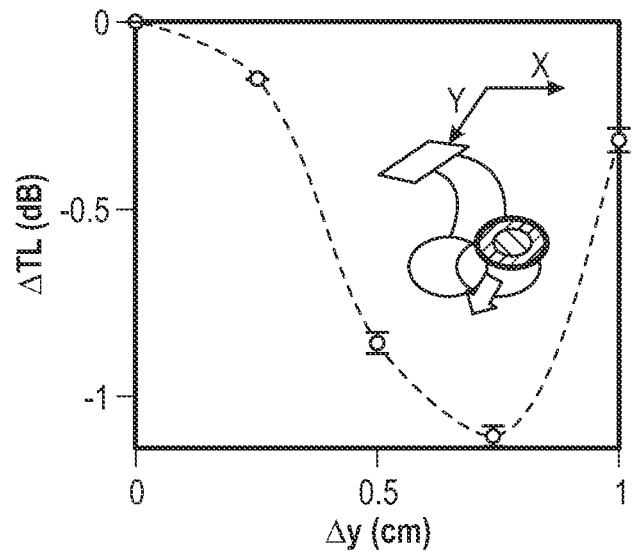
FIG. 8I is a graph showing data obtained using the resonator system.
Figure 8J:
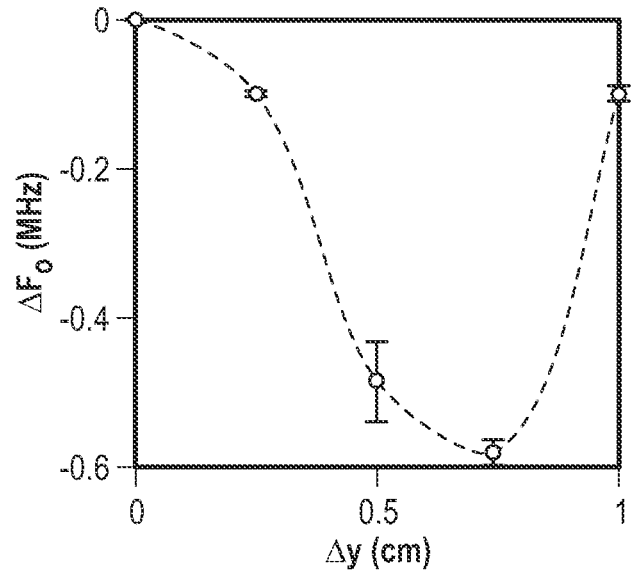
FIG. 8J is a graph showing data obtained using the resonator system.

To further understand the effect of orientation (in x, y, z, and angle dimensions) between the resonator and reader, the following protocol was used. The reader head (which contains the two looped coils which inductively couple with the resonator) occupies an area of 9×6 cm. The 5 cm diameter sticker was then oriented in the top right corner of the reader head where all analysis was performed for this study and translated in the x and y directions as well as rotated. The results show major changes (>10 dB) in the x direction and with increasing angle for TL with corresponding changes in frequency also being large with >4 MHz (FIGS. 8e-h). Less severe changes were found in the y direction with changes <1.2 dB for TL and <0.7 MHz for frequency (FIGS. 8i-j), however these deviations are relatively large compared to the dynamic range of the sweat sticker response to different conductivities and distance filled. The z direction was also analyzed with responses very similar to angular changes (see FIG. 7c).

This Example presents an initial prototype of a wireless resonant sweat sensor for monitoring undercoat/PPE perspiration. The sensor demonstrates the ability to monitor both sweat conductivity and sweat rate using the same transmission loss parameter. However, limitations still exist that need to be addressed before a human study is conducted to test sweat collection on body, under PPE or other garments. Although the effect of garment thickness on sweat conductivity response can be corrected through a linear offset relation, the effect of sweat rate does not have simple correction factor. Instead, the sensor must be calibrated through different thicknesses and types of material before use. Other limitations are highlighted in the initial performance study of resonators placed on the body and scanned after repositioning. This data demonstrates the importance of carefully re-positioning the reader and sensor in the same orientation with one another between consecutive measurements, which validates previously known phenomena involving inductively coupled systems. In order to achieve consistent orientation using the portable VNA reader, two possible strategies could be employed. One strategy would be to guide the reader into the same orientation for each scan, such as with mechanical tabs, aligning magnets, or with embedded hall sensors with activation when properly aligned. Another strategy could be employing an embedded array of resonant sensors to correct for positional changes. Alternatively, the frequency and TL dynamic range could be increased by changing the proximity of the microfluidic channel with respect to the resonator. The EM fields produced by the resonator weaken rapidly as a function of distance, and the current separation distance of 0.75 mm between the fluid and resonator coil is quite significant considering this is a near field application. This strategy of increasing the sensor signal would provide a more robust mitigation strategy than assuring proper orientation alone. Likely a combination of these strategies will be the most robust to implement before doing a large scale human trial of the sweat analysis sticker.

The Example has demonstrated a passive (no on-board power) wearable sweat rate and sweat conductivity sensor that can be measured wirelessly through clothing or PPE without the need for circuit boards. The sensor has a unique orthogonal response, which transduces the conductivity of the sweat through changes in transmission loss magnitude and sweat rate through rate of change of resonant frequency. In particular, the sweat sensor can robustly transduce the sweat conductivity through any non-metal PPE or clothing when accounting for the thickness of the material. These data were collected using a low cost (<$500) portable VNA reader. The single use sensor could be used to determine local sweat loss through multiple scans over perspiration period. The resonant sticker can also be interrogated through thick, opaque PPE with potential applications in monitoring sweat loss and hydration in firefighters during firefighting activities. These stickers could also be further designed to selectively monitor biomarkers in sweat (electrolytes, metabolites, and peptides) which would fill a need for a more sensitive sensor to monitor sweat biomarkers in situ.

Materials

Copper coated polyimide (DuPont Pyralux) for the flexible planar spiral resonators was purchased from Adafruit (35 µm copper layer, 25 µm polyimide layer). An indelible marker mask in the form of an Archimedean spiral was applied to pyralux using an X-Y plotter (Silhouette Curio). The resonator had an outer diameter of 40 mm and pitch of 1.2 mm and was designed in InkScape. These dimensions were chosen so that the resonator frequency of the bare resonator would be ~85 MHz which is below the upper frequency limit (250 MHz) of the portable VNA (MetroVNA). Copper was chemically etched around the mask using $H_2O_2$/HCl solution in a 2:1 volume ratio. Finally, the indelible mask was removed using acetone and air dried. The final resonator was then adhered to a microfluidic chip using acrylic adhesive.

PDMS (Dow Sylguard 184) for flexible microfluidic chips was purchased from Ellsworth Adhesives. The microfluidic chips were fabricated via laser ablation using a craft laser cutter (GlowForge Plus). Designs were made in InkScape and saved in a scalable vector graphics format to ensure vector mode operation of the laser cutter. Models for the depth and width of the channels were developed by cutting linear channels into PDMS with varying laser cutter powers and speeds settings between 8-24 W and between 0.008-0.04 m/s respectively. A total of 88 channels were analyzed with 22 different settings with 4 replicates per setting. The widths and depths of the linear channels were determined with an Olympus DSX110 3D microscope. The data collected was then used to fit linear models for depth and width of laser ablated channels as a function of cutting speed and laser power. The microfluidic chip made for the sweat analysis sticker was fabricated in PDMS (thickness 1 mm) with using 0.024 m/s cutting speed and 16 W laser power.

The laser ablated channels were then bonded and sealed with another layer of PDMS (thickness 1 mm) using a plasma bonding process. Both layers of PDMS were treated in a plasma treated for 30 seconds in $O_2$, plasma (plasma Etch PE-25). The pieces were then immediately placed together and bonded using finger pressure followed by a baking period in an oven at 60° C. for 10 minutes. Bonded channels were than adhered to a resonator using acrylic adhesive (thickness 100 µm) for a total sensor thickness of 2.16 mm.

NaCl used for all experiments was purchased from Sigma Aldrich. Salt solutions between 0.01 M and 0.1 M as this is the biologically relevant range of normal NaCl concentrations in sweat, Conductivity of the solutions could be calculated by taking the product of the molar conductivity, the concentration, and the activity coefficient of NaCl solution which can be calculated from the Debye-Huckel limiting law using values of molar conductivities found in and complex permittivity. The associated conductivities of the NaCl solutions prepared equaled ~1-10 mS/cm which was consistent with sweat conductivities reported in the literature. These solutions were used as 'artificial' sweat solutions to calibrate the sweat sticker to varying conductivities of sweat and to distance fluid traveled in channel.

Channels were filled using a syringe pump (Chemyx Fusion 100) attached to the sticker via tygon tubing (ID ⅛"). In order to visually determine the distance filled indelible ink marks were placed on the microfluidic chip at one-eighth turns at which data points were taken. For both the conductivity and distance filled experiments the chip was filled at one-eighth turn increments. After each fill point, the resonator was interrogated by the VNA as detailed below. For the effect of conductivity on TL the channels were completely filled with conductive solutions between 0.01-0.1 mol/L NaCl before each data point was taken.

The effect of bending on the cross sectional area of the laser ablated channels was determined by bending cut channels around a curved block of known geometry and taking images of channel cross sections with the Olympus DSX110 digital microscope. Images were subsequently analyzed in MatLab using the image Segmenter app to determine cross sectional area. A straight edged block and three curved blocks with decreasing radius of curvature (for a sharper bend) were used. For each block five channels were analyzed and average and standard deviation of cross sectional area was calculated.

Cyclic fatigue testing was also performed to determine effect of cyclic bending on sensor performance. The sensor was elastically deformed repeatedly over a curved edge. Before the testing began and after every 500 cycles the frequency shift response was taken by filling the sensor with 0.01 mon NaCl until 2000

The human study was conducted with approval and in accordance with the Iowa State University Institutional Review Board. Written informed consent was received from all participants before experiments were performed. Written consent was obtained separately for photographs of subjects used in figures for this study. The population of participants consisted of males ages 18-30 with a BMI under 30. Resonators used for the human study had 40 mm outer diameter and pitch of 1.2 mm with an inner diameter of 10 mm. Participants arrived to the kinesiology testing facility and were outfitted with resonant sensors. Resonators were attached to the body using Tegaderm (3M) and were placed on the forearm, stomach, lower back, thigh, and calf of participants. Five scans were taken for each data point to determine the noise of the signal. The average and standard deviations of these scans were calculated and reported from the five resonant sensors on four subjects.

The effect of x, y, z, and angle orientation of the reader antenna and resonator on the TL output were measured by changing the orientation between the reader and resonator. For the x and y direction this was done by manually moving the resonator across the reader head in either the x or y directions between scans. To accurately measure the effect distance displacement a grid printed on paper was taped onto the reader head. For the z direction the resonator was fixed stationary on the lab bench and the reader was attached to a vertical translation stage (Melles Griot) and raised between each scan. The distance raised was measured using scale on the vertical translation stage. For angle orientation the resonator was again fixed stationary on the lab bench and the reader was attached to a rotating lab clamp. The angle between the reader and resonator was increased between each scan with the angle measured using a protractor.

A portable VNA (MetroVNA Deluxe 250 MHz) was used for all experiments performed in this study. The VNA was transformed into a resonator reader by connecting it to a custom holder made out of a 3D printed holder with a dual-loop coil antenna. The portable VNA was interfaced with the vnaJ software (vnaj.dl2sba.com) to attain and store data. When excited with RF power from the VNA, the reader antenna generates an electromagnetic field (EM field) that inductively couples with the resonator. The software captures the inphase and quadrature of the RF signal and uses this information to calculate the TL of the device under test, e.g. the resonator and reader antenna. The TL data was analyzed using a script written in MatLab, which fit a quadratic model to the peak of the bode plot and then reported the associated TL magnitude and frequency ($f_o$). To minimize noise five scans were taken and averaged for each measurement.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Additional Embodiments

The following exemplary embodiments are provided, the numbering of which is not to be construed as designating levels of importance:

Embodiment 1 provides a resonator system for detecting perspiration, the system comprising:
a resonator comprising:
an electronically conductive segment;
a polymeric component coating at least a portion of the electronically conductive segment; and
a fluidic channel component positioned adjacent to the polymeric component and comprising a microfluidic channel.

Embodiment 2 provides the resonator system of Embodiment 1, wherein the electronically conductive segment comprises copper.

Embodiment 3 provides the resonator system of any one of Embodiments 1 or 2, wherein a profile of the conductive segment is an Archimedean spiral comprising one or more rings spaced relative to one another.

Embodiment 4 provides the resonator system of any one of Embodiments 1-3, wherein a pitch of the electronically conductive segment is in a range of from about 0.1 mm to about 10 mm.

Embodiment 5 provides the resonator system of any one of Embodiments 1-4, wherein the largest dimension perpendicular to the longitudinal direction of the electronically conductive segment is in a range of from about 5 mm to about 100 mm.

Embodiment 6 provides the resonator system of any one of Embodiments 1-5, wherein the polymeric component coats from about 10 percent surface area to about 70 percent surface area of the electronically conductive segment.

Embodiment 7 provides the resonator system of any one of Embodiments 1-6, wherein the polymeric component comprises a polyimide.

Embodiment 8 provides the resonator system of Embodiment 7, wherein the polyimide comprises a repeating unit having the structure according to Formula 1:

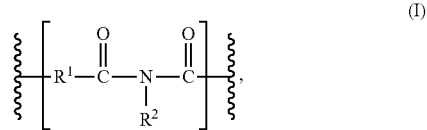

wherein
$R^1$ is chosen from —O—, —NH—, and substituted or unsubstituted ($C_1$-$C_{20}$)hydrocarbyllene; and
$R^2$ is chosen from —H, —OH, and substituted or unsubstituted ($C_1$-$C_{20}$)hydrocarbyl.

Embodiment 9 provides the resonator system of any one of Embodiments 1-8, wherein the microfluidic channel is adapted to receive perspiration.

Embodiment 10 provides the resonator system of any one of Embodiments 1-9, wherein a profile of the microfluidic channel is an Archimedean spiral.

Embodiment 11 provides the resonator system of any one of Embodiments 1-10, further comprising a patch adapted to be adhered to a user.

Embodiment 12 provides the resonator system of any one of Embodiments 1-11, further comprising a garment to which the resonator system is attached.

Embodiment 13 provides the resonator system of any one of Embodiments 1-12, further comprising a reader to detect the resonance frequency of the resonator and positioned to be in electrical communication with the resonator.

Embodiment 14 provides the resonator system of any one of Embodiments 1-13, wherein the resonator system comprises a plurality of resonators.

Embodiment 15 provides the resonator system of any one of Embodiments 1-14, further comprising an adhesive adhering the fluidic channel component to the polymeric component.

Embodiment 16 provides the resonator system of any one of Embodiments 1-15, wherein the fluidic channel component comprises polydimethylsiloxane Embodiment 17 provides the resonator system of any one of Embodiments 1-16, wherein the microfluidic channel is laser ablated.

Embodiment 18 provides the resonator system of any one of Embodiments 1-17, wherein the system is further adapted to measure a peak height of the resonance frequency.

Embodiment 19 provides the resonator system of Embodiment 18, wherein the peak height of the resonance frequency correlates an amount of electrolyte present in the perspiration.

Embodiment 20 provides the resonator system of Embodiment 19, wherein the electrolyte comprises sodium.

Embodiment 21 provides the resonator system of any one of Embodiments 18-20, wherein the system is adapted to measure the resonance frequency and the peak height of the resonance frequency simultaneously.

Embodiment 22 provides the resonator system of any one of Embodiments 1-21, further comprising polyphenyl ether disposed between the resonator and the resonator reader.

Embodiment 23 provides a method of detecting perspiration, the method comprising:
measuring a first resonance frequency of the resonator of the resonator system according to any one of Embodiments 1-22;
contacting the microfluidic channel with perspiration; and
measuring a second resonance frequency of the resonator following contacting the perspiration with the microfluidic channel.

Embodiment 24 provides the method of Embodiment 23, wherein the second resonance frequency is less than the first resonance frequency.

Embodiment 25 provides the method of any one of Embodiments 23 or 24, wherein at least one of the first resonance frequency and the second resonance frequency are in a range of from about 1 MHz to about 500 MHz.

Embodiment 26 provides the method of any one of Embodiments 23-25, wherein at least one of the first resonance frequency and the second resonance frequency are in a range of from about 1 MHz to about 100 MHz.

Embodiment 27 provides the method of any one of Embodiments 23-26, wherein the perspiration fills the microfluidic channel.

Embodiment 28 provides the method of Embodiment 27, further comprising determining a concentration of an electrolyte in the perspiration.

Embodiment 29 provides the method of Embodiment 28, wherein determining the presence of the perspiration comprises measuring a plurality of resonance frequencies over a predetermined amount of time.

Embodiment 30 provides the method of any one of Embodiments 23-29, further comprising placing the resonator system in contact with a user.

Embodiment 31 provides the method of any one of Embodiments 23-30, further comprising measuring a peak height of the resonance frequency to determine the concentration of an electrolyte in the perspiration.

Embodiment 32 provides the method of Embodiment 31, wherein the peak height of the resonance frequency is measured simultaneously with the resonance frequency.

Embodiment 33 provides a method of making the resonator system according to any one of Embodiments 1-32, the method comprising:
providing or receiving the electronically conductive segment at least partially coated with the polymeric component;
etching the electronically conductive segment to form a pattern therein;
adhering the polymeric component to a fluidic channel component precursor; and
forming a microfluidic channel in the fluidic channel component by laser ablation.

Embodiment 34 provides the method of Embodiment 33, further comprising printing the pattern on a surface of the electronically conductive segment prior to etching.

Embodiment 35 provides the method of any one of Embodiments 33 or 34, wherein etching comprises at least partially immersing the electronically conductive segment in a solution comprising an etchant.

What is claimed is:

1. A system for detecting perspiration, the system comprising:
a sensing component comprising a resonator comprising:
a platform comprising an electronically conductive segment having a spiral shape, having pitch in a range of from about 0.1 mm to about 10 mm;
a polymeric component coating at least a portion of the electronically conductive segment; and
a microfluidic channel component defined by the platform and positioned to contact the polymeric component and
a reader to detect the resonance frequency of the resonator and positioned to be in electrical communication with the resonator.

2. The system of claim 1 wherein the polymeric component comprises a polyimide.

3. The system of claim 2, wherein the polyimide comprises a repeating unit having the structure according to Formula I:

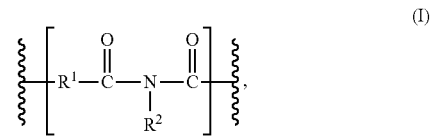

wherein
$R^1$ is chosen from —O—, —NH—, and substituted or unsubstituted $(C_1$-$C_{20})$ hydrocarbylene; and
$R^2$ is chosen from —H, —OH, and substituted or unsubstituted $(C_1$-$C_{20})$ hydrocarbyl.

4. The system of claim 1, wherein the microfluidic channel is adapted to receive perspiration.

5. The system of claim 4, wherein a profile of the microfluidic channel is an Archimedean spiral.

6. The system of claim 1, further comprising a patch adapted to be adhered to a user.

7. The system of claim 1, further comprising a garment to which the resonator system is attached.

8. The system of claim 1, wherein the microfluidic channel component comprises polydimethylsiloxane.

9. The system of claim 1, wherein the system is further adapted to measure a peak height of the resonance frequency.

10. The system of claim 9, wherein the peak height of the resonance frequency correlates an amount of electrolyte present in the perspiration.

11. The system of claim 10, wherein the electrolyte comprises sodium.

12. The system of claim 10, wherein the system is adapted to measure the resonance frequency and the peak height of the resonance frequency simultaneously.

13. The resonator system of claim 1, wherein the spiral shape comprises an Archimedean spiral.

14. A method of detecting perspiration, the method comprising:
   measuring a first resonance frequency of a system with a resonance reader,
   contacting a microfluidic channel of the system with perspiration; and
   measuring a second resonance frequency of the resonator system following contacting the perspiration with the microfluidic channel with the resonance reader, wherein the system comprises:
   sensing component comprising a resonator comprising:
      a platform comprising an electronically conductive segment having a spiral shape, having pitch in a range of from about 0.1 mm to about 10 mm;
      a polymeric component coating at least a portion of the electronically conductive segment; and
   the microfluidic channel is defined by the platform.

15. The method of claim 14, wherein the second resonance frequency is less than the first resonance frequency.

16. The method of claim 15, wherein at least one of the first resonance frequency and the second resonance frequency are in a range of from about 1 MHz to about 500 MHz.

17. The method of claim 14, further comprising measuring a peak height of the resonance frequency to determine the concentration of an electrolyte in the perspiration.

* * * * *